(12) United States Patent
Schomacker et al.

(10) Patent No.: US 6,818,903 B2
(45) Date of Patent: Nov. 16, 2004

(54) METHOD AND APPARATUS FOR IDENTIFYING SPECTRAL ARTIFACTS

(75) Inventors: Kevin T. Schomacker, Maynard, MA (US); Thomas Meese, Brookline, MA (US); Michael Ouradnik, Wayland, MA (US); John Flanagan, Holbrook, MA (US); Harry Gao, Stoneham, MA (US)

(73) Assignee: Medispectra, Inc., Lexington, MA (US)

( * ) Notice: Subject to any disclaimer, the term of this patent is extended or adjusted under 35 U.S.C. 154(b) by 78 days.

(21) Appl. No.: 10/243,535

(22) Filed: Sep. 13, 2002

(65) Prior Publication Data

US 2004/0007674 A1 Jan. 15, 2004

Related U.S. Application Data

(60) Provisional application No. 60/394,696, filed on Jul. 9, 2002.

(51) Int. Cl.⁷ .................................................. G01T 1/10
(52) U.S. Cl. .................................. 250/458.1; 250/461.2
(58) Field of Search ........................... 250/458.1, 461.2, 250/341.1, 341.2, 341.7, 341.8, 317

(56) References Cited

U.S. PATENT DOCUMENTS

| | | | |
|---|---|---|---|
| 3,013,467 A | 12/1961 | Minsky | 88/14 |
| 3,632,865 A | 1/1972 | Haskell et al. | 178/6 |
| 3,809,072 A | 5/1974 | Ersek et al. | 128/23 |
| 3,890,462 A | 6/1975 | Limb et al. | 178/6.8 |
| 3,963,019 A | 6/1976 | Quandt | 128/2 |
| D242,393 S | 11/1976 | Bauman | D83/12 R |
| D242,396 S | 11/1976 | Bauman | D83/12 R |
| D242,397 S | 11/1976 | Bauman | D83/12 R |
| D242,398 S | 11/1976 | Bauman | D83/12 R |
| 4,017,192 A | 4/1977 | Rosenthal | 356/201 |
| 4,071,020 A | 1/1978 | Pugliese | 128/2 |
| 4,198,571 A | 4/1980 | Sheppard | 250/571 |
| 4,218,703 A | 8/1980 | Netravali et al. | 358/136 |
| 4,254,421 A | 3/1981 | Kreutel, Jr. | 343/754 |
| 4,273,110 A | 6/1981 | Groux | 128/6 |
| 4,357,075 A | 11/1982 | Hunter | 350/294 |
| 4,397,557 A | 8/1983 | Herwig et al. | 356/342 |

(List continued on next page.)

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |

(List continued on next page.)

OTHER PUBLICATIONS

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

(List continued on next page.)

*Primary Examiner*—David Porta
*Assistant Examiner*—Christine Sung
(74) *Attorney, Agent, or Firm*—Testa, Hurwitz & Thibeault, LLP

(57) ABSTRACT

The invention provides an apparatus and methods for determining whether spectral data obtained from a region of a tissue sample are affected by an artifact. Artifacts include, for example, lighting artifacts such as glare and shadow and obstruction artifacts, such as blood, a speculum, a smoke tube, or other obstruction. Additionally, the invention provides an apparatus and methods for obtaining redundant spectral data of a given region of a sample. A redundant set of spectral data is useful where one or more artifacts affect some but not all sets of the spectral data, such that the redundant set of data is unaffected by the artifact and is representative of the tissue. An embodiment of the invention comprises using representative spectral data in diagnosing a condition of a region of tissue.

39 Claims, 18 Drawing Sheets

(5 of 18 Drawing Sheet(s) Filed in Color)

U.S. PATENT DOCUMENTS

| | | |
|---|---|---|
| 4,549,229 A | 10/1985 | Nakano et al. .................. 360/8 |
| 4,646,722 A | 3/1987 | Silverstein et al. ............. 128/4 |
| 4,662,360 A | 5/1987 | O'Hara et al. .................. 128/9 |
| 4,733,063 A | 3/1988 | Kimura et al. ................ 250/201 |
| 4,741,326 A | 5/1988 | Sidall et al. .................... 128/4 |
| 4,753,530 A | 6/1988 | Knight et al. .................. 356/73 |
| 4,768,513 A | 9/1988 | Suzuki ......................... 128/634 |
| 4,800,571 A | 1/1989 | Konishi ......................... 375/10 |
| 4,844,617 A | 7/1989 | Kelderman et al. ........... 356/372 |
| 4,845,352 A | 7/1989 | Benschop .................... 250/201 |
| 4,852,955 A | 8/1989 | Doyle et al. ................. 350/1.2 |
| 4,877,033 A | 10/1989 | Seitz, Jr. ................ 128/660.05 |
| 4,878,485 A | 11/1989 | Adair ............................. 128/6 |
| 4,891,829 A | 1/1990 | Deckman et al. .............. 378/4 |
| 4,930,516 A | 6/1990 | Alfano et al. ................ 128/665 |
| 4,945,478 A | 7/1990 | Merickel et al. ........ 364/413.22 |
| 4,965,441 A | 10/1990 | Picard ...................... 250/201.3 |
| 4,972,258 A | 11/1990 | Wolf et al. .................... 358/93 |
| 4,974,580 A | 12/1990 | Anapliotis ...................... 128/4 |
| 4,979,498 A | 12/1990 | Oneda et al. ................... 128/6 |
| 4,997,242 A | 3/1991 | Amos ........................ 350/6.91 |
| 5,003,979 A | 4/1991 | Merickel et al. ........ 364/413.22 |
| 5,011,243 A | 4/1991 | Doyle et al. ................. 350/1.2 |
| 5,022,757 A | 6/1991 | Modell ........................ 356/318 |
| 5,028,802 A | 7/1991 | Webb et al. ................. 250/571 |
| 5,032,720 A | 7/1991 | White ......................... 250/236 |
| 5,034,613 A | 7/1991 | Denk et al. ............... 250/458.1 |
| 5,036,853 A | 8/1991 | Jeffcoat et al. .............. 128/634 |
| 5,042,494 A | 8/1991 | Alfano ........................ 128/665 |
| 5,048,946 A | 9/1991 | Sklar et al. .................. 351/206 |
| 5,054,926 A | 10/1991 | Dabbs et al. ................ 356/345 |
| 5,065,008 A | 11/1991 | Hakamata et al. ........... 250/216 |
| 5,071,246 A | 12/1991 | Blaha et al. ................. 351/221 |
| 5,074,306 A | 12/1991 | Green et al. ................ 128/664 |
| 5,083,220 A | 1/1992 | Hill ............................. 359/234 |
| 5,091,652 A | 2/1992 | Mathies et al. ........... 250/458.1 |
| 5,101,825 A | 4/1992 | Gravenstein et al. ........ 128/633 |
| 5,120,953 A | 6/1992 | Harris ....................... 250/227.2 |
| 5,122,653 A | 6/1992 | Ohki ........................... 250/216 |
| 5,132,526 A | 7/1992 | Iwasaki .................... 250/201.3 |
| 5,139,025 A | 8/1992 | Lewis et al. ................. 128/665 |
| 5,154,166 A | 10/1992 | Chikama ........................ 128/4 |
| 5,159,919 A | 11/1992 | Chikama ........................ 128/4 |
| 5,161,053 A | 11/1992 | Dabbs ......................... 359/384 |
| 5,162,641 A | 11/1992 | Fountain .................. 250/201.2 |
| 5,162,941 A | 11/1992 | Favro et al. ................. 359/386 |
| 5,168,157 A | 12/1992 | Kimura ....................... 250/234 |
| 5,192,980 A | 3/1993 | Dixon et al. ................. 356/326 |
| 5,193,525 A | 3/1993 | Silverstein et al. ............. 128/4 |
| RE34,214 E | 4/1993 | Carlsson et al. .............. 358/93 |
| 5,199,431 A | 4/1993 | Kittrell et al. ............... 128/634 |
| 5,201,318 A | 4/1993 | Rava et al. .................. 128/665 |
| 5,201,908 A | 4/1993 | Jones ............................. 128/4 |
| 5,203,328 A | 4/1993 | Samuels et al. ............. 128/633 |
| 5,225,671 A | 7/1993 | Fukuyama .................. 250/216 |
| 5,235,457 A | 8/1993 | Lichtman et al. ........... 359/368 |
| 5,237,984 A | 8/1993 | Williams, III et al. .......... 128/4 |
| 5,239,178 A | 8/1993 | Derndinger et al. ........ 250/234 |
| 5,248,876 A | 9/1993 | Kerstens et al. ............. 250/561 |
| 5,253,071 A | 10/1993 | MacKay ..................... 358/222 |
| 5,257,617 A | 11/1993 | Takahashi ...................... 128/4 |
| 5,260,569 A | 11/1993 | Kimura ....................... 250/234 |
| 5,260,578 A | 11/1993 | Bliton et al. ............. 250/461.1 |
| 5,261,410 A | 11/1993 | Alfano et al. ................ 128/665 |
| 5,262,646 A | 11/1993 | Booker et al. ............... 250/341 |
| 5,274,240 A | 12/1993 | Mathies et al. ........... 250/458.1 |
| 5,284,149 A | 2/1994 | Dhadwal et al. ............. 128/665 |
| 5,286,964 A | 2/1994 | Fountain .................. 250/201.2 |
| 5,289,274 A | 2/1994 | Kondo ........................ 348/208 |
| 5,294,799 A | 3/1994 | Aslund et al. ............ 250/458.1 |
| 5,296,700 A | 3/1994 | Kumagai ..................... 250/216 |
| 5,303,026 A | 4/1994 | Strobl et al. ................. 356/318 |
| 5,306,902 A | 4/1994 | Goodman ................. 250/201.3 |
| 5,313,567 A | 5/1994 | Civanlar et al. ............. 395/124 |
| 5,319,200 A | 6/1994 | Rosenthal et al. ........... 250/341 |
| 5,321,501 A | 6/1994 | Swanson et al. ............ 356/345 |
| 5,324,979 A | 6/1994 | Rosenthal ............... 250/504 R |
| 5,325,846 A | 7/1994 | Szabo ............................ 128/4 |
| 5,329,352 A | 7/1994 | Jacobsen ..................... 356/301 |
| 5,337,734 A | 8/1994 | Saab .............................. 128/4 |
| 5,343,038 A | 8/1994 | Nishiwaki et al. .......... 250/234 |
| 5,345,306 A | 9/1994 | Ichimura et al. ............ 356/346 |
| 5,345,941 A | 9/1994 | Rava et al. .................. 128/665 |
| 5,349,961 A | 9/1994 | Stoddart et al. ............. 128/665 |
| 5,398,685 A | 3/1995 | Wilk et al. ................ 128/653.1 |
| 5,402,768 A | 4/1995 | Adair ............................. 128/4 |
| 5,406,939 A | 4/1995 | Bala ............................... 128/4 |
| 5,413,092 A | 5/1995 | Williams, III et al. ......... 128/4 |
| 5,413,108 A | 5/1995 | Alfano ........................ 128/665 |
| 5,415,157 A | 5/1995 | Welcome ....................... 128/4 |
| 5,418,797 A | 5/1995 | Bashkansky et al. .......... 372/3 |
| 5,419,311 A | 5/1995 | Yabe et al. ..................... 128/4 |
| 5,419,323 A | 5/1995 | Kittrell et al. ............... 128/653 |
| 5,421,337 A | 6/1995 | Richards-Kortum et al. ........................... 128/665 |
| 5,421,339 A | 6/1995 | Ramanujam et al. ....... 128/665 |
| 5,424,543 A | 6/1995 | Dombrowski et al. ...... 250/330 |
| 5,450,857 A | 9/1995 | Garfield et al. ............. 128/778 |
| 5,451,931 A | 9/1995 | Muller et al. ................ 340/630 |
| 5,458,132 A | 10/1995 | Yabe et al. ..................... 128/4 |
| 5,458,133 A | 10/1995 | Yabe et al. ................... 600/121 |
| 5,467,767 A | 11/1995 | Alfano et al. ................ 128/665 |
| 5,469,853 A | 11/1995 | Law et al. ............. 128/662.06 |
| 5,477,382 A | 12/1995 | Pernick ....................... 359/559 |
| 5,480,775 A | 1/1996 | Ito et al. ....................... 435/7.2 |
| 5,493,444 A | 2/1996 | Khoury et al. ............... 359/559 |
| 5,496,259 A | 3/1996 | Perkins ........................ 600/124 |
| 5,507,295 A | 4/1996 | Skidmore .................... 600/121 |
| 5,516,010 A | 5/1996 | O'Hara et al. ............... 600/122 |
| 5,519,545 A | 5/1996 | Kawahara ..................... 360/46 |
| 5,529,235 A | 6/1996 | Boiarski et al. .......... 227/175.1 |
| 5,536,236 A | 7/1996 | Yabe et al. .................. 600/125 |
| 5,545,121 A | 8/1996 | Yabe et al. .................. 600/121 |
| 5,551,945 A | 9/1996 | Yabe et al. .................. 600/122 |
| 5,556,367 A | 9/1996 | Yabe et al. .................. 600/124 |
| 5,562,100 A | 10/1996 | Kittrell et al. ............... 128/665 |
| 5,579,773 A | 12/1996 | Vo-Dinh et al. ............ 128/665 |
| 5,582,168 A | 12/1996 | Samuels et al. ............. 128/633 |
| 5,587,832 A | 12/1996 | Krause ........................ 359/385 |
| 5,596,992 A | 1/1997 | Haaland et al. .............. 128/664 |
| 5,599,717 A | 2/1997 | Vo-Dinh ....................... 436/63 |
| 5,609,560 A | 3/1997 | Ichikawa et al. ............ 600/101 |
| 5,612,540 A | 3/1997 | Richards-Kortum et al. ........................ 250/461.2 |
| 5,623,932 A | 4/1997 | Ramanujam et al. ....... 128/665 |
| 5,647,368 A | 7/1997 | Zeng et al. .................. 128/665 |
| 5,662,588 A | 9/1997 | Iida .............................. 600/121 |
| 5,685,822 A | 11/1997 | Harhen ........................ 600/125 |
| 5,690,106 A | 11/1997 | Bani-Hashemi et al. . 128/653.1 |
| 5,693,043 A | 12/1997 | Kittrell et al. ................ 606/15 |
| 5,695,448 A | 12/1997 | Kimura et al. ............... 600/121 |
| 5,697,373 A | 12/1997 | Richards-Kortum et al. ........................... 128/664 |
| 5,699,795 A | 12/1997 | Richards-Kortum et al. ........................... 128/634 |
| 5,704,892 A | 1/1998 | Adair .......................... 600/121 |
| 5,707,343 A | 1/1998 | O'Hara et al. ............... 600/121 |
| 5,713,364 A | 2/1998 | DeBaryshe et al. ......... 128/664 |
| 5,717,209 A | 2/1998 | Bigman et al. ......... 250/339.12 |
| 5,730,701 A | 3/1998 | Furukawa et al. ........... 600/127 |
| 5,733,244 A | 3/1998 | Yasui et al. .................. 600/127 |

| | | | |
|---|---|---|---|
| 5,735,276 A * | 4/1998 | Lemelson | 600/407 |
| 5,746,695 A | 5/1998 | Yasui et al. | 600/127 |
| 5,768,333 A | 6/1998 | Abdel-Mottaleb | 378/37 |
| 5,769,792 A | 6/1998 | Palcic et al. | 600/477 |
| 5,773,835 A | 6/1998 | Sinofsky | 250/462.1 |
| 5,791,346 A | 8/1998 | Craine et al. | 128/653 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,813,987 A | 9/1998 | Modell et al. | 600/473 |
| 5,817,015 A | 10/1998 | Adair | 600/121 |
| 5,830,146 A | 11/1998 | Skladnev et al. | 600/478 |
| 5,833,617 A | 11/1998 | Hayashi | 600/476 |
| 5,840,035 A | 11/1998 | Heusmann et al. | 600/47 |
| 5,842,995 A | 12/1998 | Mahadevan-Jansen et al. | 600/473 |
| 5,855,551 A | 1/1999 | Sklandnev et al. | 600/372 |
| 5,860,913 A | 1/1999 | Yamaya et al. | 600/127 |
| 5,863,287 A | 1/1999 | Segawa | 600/121 |
| 5,865,726 A | 2/1999 | Katsurada et al. | 600/127 |
| 5,876,329 A | 3/1999 | Harhen | 600/125 |
| 5,920,399 A | 7/1999 | Sandison et al. | 356/418 |
| 5,921,926 A | 7/1999 | Rolland et al. | 600/407 |
| 5,929,985 A | 7/1999 | Sandison et al. | 365/318 |
| 5,931,779 A | 8/1999 | Arakaki et al. | 600/310 |
| 5,938,617 A | 8/1999 | Vo-Dinh | 600/476 |
| 5,941,834 A | 8/1999 | Skladnev et al. | 600/587 |
| 5,983,125 A | 11/1999 | Alfano et al. | 600/473 |
| 5,989,184 A | 11/1999 | Blair | 600/167 |
| 5,991,653 A | 11/1999 | Richards-Kortum et al. | 660/475 |
| 5,995,645 A | 11/1999 | Soenksen et al. | 382/133 |
| 6,021,344 A | 2/2000 | Lui et al. | 600/476 |
| 6,058,322 A | 5/2000 | Nishikawa et al. | 600/408 |
| 6,069,689 A | 5/2000 | Zeng et al. | 356/773 |
| 6,091,985 A | 7/2000 | Alfano et al. | 600/476 |
| 6,095,982 A | 8/2000 | Richards-Kortum et al. | 600/476 |
| 6,096,065 A | 8/2000 | Crowley | 607/88 |
| 6,099,464 A | 8/2000 | Shimizu et al. | 600/104 |
| 6,104,945 A | 8/2000 | Modell et al. | 600/473 |
| 6,119,031 A | 9/2000 | Crowley | 600/407 |
| 6,124,597 A * | 9/2000 | Shehada et al. | 250/461.2 |
| 6,146,897 A | 11/2000 | Cohenford et al. | 436/63 |
| 6,169,817 B1 | 1/2001 | Parker et al. | 382/131 |
| 6,208,887 B1 | 3/2001 | Clarke | 600/476 |
| 6,241,662 B1 | 6/2001 | Richards-Kortum et al. | 600/310 |
| 6,243,601 B1 | 6/2001 | Wist | 600/473 |
| 6,246,471 B1 | 6/2001 | Jung et al. | 356/73 |
| 6,246,479 B1 | 6/2001 | Jung et al. | 356/419 |
| 6,285,639 B1 | 9/2001 | Maenza et al. | 369/47.28 |
| 6,312,385 B1 | 11/2001 | Mo et al. | 600/443 |
| 6,317,617 B1 | 11/2001 | Gilhuijs et al. | 600/408 |
| D453,832 S | 2/2002 | Morrell et al. | D24/138 |
| D453,962 S | 2/2002 | Morrell et al. | D24/138 |
| D453,963 S | 2/2002 | Morrell et al. | D24/138 |
| D453,964 S | 2/2002 | Morrell et al. | D24/138 |
| 6,377,842 B1 | 4/2002 | Pogue et al. | 600/478 |
| 6,385,484 B2 | 5/2002 | Nordstrom et al. | 600/476 |
| 6,411,835 B1 | 6/2002 | Modell et al. | 600/407 |
| 6,411,838 B1 | 6/2002 | Nordstrom et al. | 600/476 |
| D460,821 S | 7/2002 | Morrell et al. | D24/138 |
| 6,421,553 B1 | 7/2002 | Costa et al. | 600/476 |
| 6,427,082 B1 | 7/2002 | Nordstrom et al. | 600/476 |
| 6,571,118 B1 | 5/2003 | Utzinger et al. | 600/476 |
| 6,574,502 B2 * | 6/2003 | Hayashi | 600/476 |
| 2002/0007122 A1 | 1/2002 | Kaufman et al. | 600/476 |
| 2002/0007123 A1 | 1/2002 | Balas et al. | 600/476 |
| 2002/0127735 A1 | 9/2002 | Kaufman et al. | 600/436 |
| 2002/0177777 A1 | 11/2002 | Nordstrom et al. | 600/475 |
| 2002/0183626 A1 | 12/2002 | Nordstrom et al. | 600/476 |
| 2003/0095721 A1 | 5/2003 | Clune et al. | 382/294 |
| 2003/0144585 A1 | 7/2003 | Kaufman et al. | 600/407 |

FOREIGN PATENT DOCUMENTS

| | | | |
|---|---|---|---|
| EP | 0 444 689 A2 | 9/1991 | |
| EP | 0 474 264 | 3/1992 | |
| EP | 0 641 542 | 3/1995 | |
| EP | 0 689 045 A1 | 12/1995 | |
| EP | 0 737 849 A2 | 10/1996 | |
| JP | 08-280602 | 10/1996 | A61B/1/00 |
| WO | WO 92/19148 | 11/1992 | |
| WO | WO 93/14688 | 8/1993 | |
| WO | WO 94/26168 | 11/1994 | |
| WO | WO 95/00067 | 1/1995 | A61B/1/22 |
| WO | WO 95/04385 | 2/1995 | |
| WO | WO 97/05473 | 2/1997 | |
| WO | WO 998/30889 | 2/1997 | |
| WO | WO 97/48331 | 12/1997 | |
| WO | WO 98/05253 | 2/1998 | |
| WO | WO 98/24369 | 6/1998 | |
| WO | WO 98/41176 | 9/1998 | |
| WO | WO 99/18847 | 4/1999 | |
| WO | WO 99/20313 | 4/1999 | |
| WO | WO 99/20314 | 4/1999 | |
| WO | WO 99/47041 | 9/1999 | |
| WO | WO 99/57507 | 11/1999 | |
| WO | WO 99/57529 | 11/1999 | |
| WO | WO 00/15101 | 3/2000 | |
| WO | WO 00/59366 | 10/2000 | |

OTHER PUBLICATIONS

Althof et al. (1997), "A rapid and automatic image registration algorithm with subpixel accurace," *IEEE Transactions on Medical Imaging,* 16(3):308–316.

Anderson (1994), "Confocal Laser Microscopes See A Wider Field of Application", *Laser Focus World,* pp. 83–86.

Aström et al. (1999), "Motion estimation in image sequences using the deformation of apparent contours," *IEEE Transactions on Pattern Analysis and Machine Intelligence,* 21(2):114–127.

Balas (1997), "An Imaging Colorimeter for Noncontact Tissue Color Mapping," *IEEE Transactions on Biomedical Engineering,* 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering,* 48(1):96–104.

Balas et al. (1997), "A modular diffuse reflection and fluorescence emission imaging colorimeter for the in–vivo study of parameters related with the phototoxic effect in PDT," *SPIE,* 3191:50–57.

Balas et al. (1998), "In Vivo Assessment of Acetic Acid-Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm, Sweden, *SPIE,* vol. 3568:31–37.

Balas et al. (1999), "In Vivo Detection and Staging of Epithelial Dysplasias and Malignancies Based on the Quantitative Assessment of Acetic Acid–Tissue Interaction Kinetics." *Journal of Photochemistry and Photobiology β: Biology,* 53:153–157.

Bessey et al. (1949), "The Fluorometric measurement of the nucleotides of riboflavin and their concentration in tissues," *J. Biol. –Chem:* 180:755–769.

Bors et al. (1998), "Optical flow estimation and moving object segmentation based on median radial basis function network," *IEEE Transactions on Image Processing,* 7(5):693–702.

Bouthemy et al. (1999), "A unified approach to shot change detection and camera motion characterization," *IEEE Transactions on Circuits and Systems for Video Technology,* 9(7):1030–1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.,* 62:84R–101R.

Camus et al. (1997), "Real–time quantized optical flow," *Real–Time Imaging,* 3:71–86.

Caplier et al. (1998), "Real–time implementation of a MRF-based motion detection algorithm," *Real–Time Imaging,* 4:41–54.

Contini et al. (1989), "Colposcopy and Computer Graphics: a New Method?" *Amer. J. Obstet. Gynecol.,* 160(3):535–538.

Craine et al. (1993), "Digital Imaging Colposcopy: basic concepts and applications," *Amer. J. Obstet. Gynecol.,* 82(5):869–873.

Craine et al. (1998), "Digital imaging colposcopy: Corrected area measurements using shape–from–shading," *IEEE Transactions on Medical Imaging,* 17(6):1003–1010.

Crisp et al. (1990), "The Computerized Digital Imaging Colposcope: Future Directions," *Amer. J. Obstet. Gynecol.,* 162(6):1491–1497.

Cronjé et al. (1997), "Effects of Dilute Acetic Acid on the Cervical Smear," *Acta. Cytol.,* 41:1091–1094.

Davidovits et al. (1971), "Scanning Laser Microscope for Biological Investigations", *Applied Optics,* 10(7):1615–1619.

Dickman et al. (2001), "Identification of Cervical Neoplasia Using a Simulation of Human Vision," *Journal of Lower Genital Tract Disease,* 5(3):144–152.

Drezek et al. (1999), "Light scattering from cells: finite–difference time–domain simulations and goniometric measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.,* 182(5):1135–1139.

Dumontier et al. (1999). "Real–time DSP implementation for MRF–based video motion detection," *IEEE Transactions on Image Processing,* 8(10):1341–1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence,* 18(9):927–932.

Edebiri, A.A. (1990), "The relative significance of colposcopic discriptive appearances in the dianosis of cervical intraepithelial neoplasia," *Int. J. Gynecol. Obstet.,* 33:23–29.

Eisner et al. (1987), "Use of Cross–Correlation Function to Detect Patient Motion During Spectral Imaging," *Journal of Nuclear Medicine,* 28(1):97–101.

Ferris et al. (1998), "Colposcopy Quality Control: Establishing Colposcopy Criterion Standards for the NCI ALTS Trial Using Cervigrams," *J. Lower Genital Tract Disease,* 2(4):195–203.

Fleet et al. (1995), "Recursive Filters for Optical Flow," *IEEE Transactions on Pattern Analysis and Machine Intelligence,* 17(1):61–67.

Gao et al. (1998), "A work minimization approach to image morphing," *The Visual Computer,* 14:390–400.

Gauch (1999), "Image Segmentation and Analysis Via Multiscale Gradient Watershed Hierarchies," *IEEE Transactions on Image Processing,* 8(1):69–79.

Hall et al. (1992), "Near–Infrared Spectrophotometry: A New Dimension in Clinical Chemistry", *Clin. Chem.* 38(9):1623–1631.

Haralick (1984), "Digital Step Edges from Zero Crossing of Second Directional Derivatives," *IEEE Transactions on Pattern Analysis and Machine Intelligence,* 6(1):58–68.

Haris et al. (1998), "Hybrid Image Segmentation Using Watersheds and Fast Region Merging," *IEEE Transactions on Image Processing,* 7(12):1684–1699.

Helmhorst et al. (1987), "The accuracy of colposcopically directed biopsy in diagnosis of CIN 2/3." *Eur. J. Obstet. Gyn. Reprod. Biol.,* 24, 221–229.

Horn et al. (1981), "Determining Optical Flow," *Artificial Intelligence,* 17(1–3):185–203.

Horn et al. (1993), "Determing Optical Flow": a retrospective, *Artificial Intelligence,* 59:81–87.

Huang et al. (1979), "A fast two–dimensional median filtering algorithm," *IEEE Transactions on Acoustics, Speech, and Signal Processing,* 27(1):13–18.

Jackway (1996), "Gradient Watersheds in Morphological Scale–Space," *IEEE Transactions on Image Processing,* 5(6):913–921.

Ji et al. (2000), "Texture Analysis for Classification of Cervix Lesions," *IEEE Transactions on Medical Imaging.* 19(11):1144–1149.

Kierkegaard et al. (1995), "Association between Colposcopic Findings and Histology in Cervical Lesions: The Significance of the Size of the Lesion" *Gynecologic Oncology,* 57:66–71.

Koester (1980), "Scanning Mirror Microscope with Optical Sectioning Characteristics: Applications in Ophthalmology", *Applied Optics,* 19(11):1749–1757.

Koester, "Comparison of Optical Sectioning Methods: The Scanning Slit Confocal Microscope", *Confocal Microscope Handbook,* pp. 189–194.

Kumar et al. (1996), "Optical Flow: A Curve Evolution Approach," *IEEE Transactions on Image Processing,* 5(4):598–610.

Linde et al. (1980), An algorithm for vector quantizer design,: *IEEE Transactions on Communications,* 28(1):84–95.

MacAulay et al. (2002), "Variation of fluorescence spectroscopy during the menstrual cycle," *Optics Express,* 10(12):493–504.

MacLean A.B. (1999), "What is Acetowhite Epithelium," *Abstract Book: 10th World Congress of Cervical Pathology and Colposcopy,* Nov. 7–11, Buenos Aires, Argentina 41.

Marzetta et al. (1999), "A surprising radon transform result and its application to motion detection," *IEEE Transactions on Image Processing,* 8(8):1039–1049.

Miike et al. (1999), "Motion enhancement for preprocessing of optical flow and scientific visualization," *Pattern Recognition Letters,* 20:451–461.

Mikhail et al. (1995), "Computerized colposcopy and conservative management of cervical intraepithelial neoplasia in pregnancy," *Acta Obstet. Gynecol. Scand.,* 74:376–378.

Milanfar (1999), "Two-dimensional matched filtering for motion estimation," *IEEE Transactions on Image Processing*, 8(3) 438–444.

Mitchell et al. (1998), "Colposcopy for the diagnosis of squamous intraepithelial lesions: a meta–analysis," *Obstet. Gynecol*, 91(4):626–631.

Mycek et al. (1998), "Colonic polyp differentiation using time–resolved autofluorescence spectroscopy," *Gastrointestinal Endoscopy*, 48(4):390–394.

Nanda et al. (2000), "Accuracy of the Papanicolaou test in screening for and follow–up of cervical cytologic abnormalities: a systemic review," *Ann Intern Med.*, 132(10):810–819.

Nesi et al. (1998), "RETIMAC REalTime Motion Analysis Chip," *IEEE Transactions on Circuits and Systems–II: Analog and Digital Signal Processing*, 45(3) 361–375.

Noumeir et al. (1996), "Detection of Motion During Tomographic Aquisition by an Optical Flow Algorithm," *Computers and Biomedical Research*, 29(1):1–15.

O'Sullivan et al. (1994). "Interobserver variation in the diagnosis and grading of dyskaryosis in cervical smears: specialist cytopathologists compared with non–specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):119–131.

Pan et al. (1998), "Correlation–feedback Technique in Optical Flow Determination," *IEEE Transactions on Image Processing*, 7(7):1061–1067.

Perona et al. (1990), "Scale–space and edge detection using anisotropic diffusion," *IEEE Transactions on Pattern Analysis and Machine Intelligence*, 12(7):629–639.

Pogue et al. (2001), "Analysis of Acetic Acid–Induced Whitening of High–Grade Squamous Intraepithelial Lesions," *Journal of Biomedical Optics*, 6(4):397–403.

Radjadhyaksha et al. (2000), "Confocal microscopy of excised human skin using acetic acid and crossed polarization: rapid detection of non–melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Ramanujam et al. (1994) "In vivo diagnosis of cervical intraepithelial neoplasia using 337–nm–exited laser–induced fluorescence", *Pro. Natl. Acad. Sci. USA*, 91:10193–10197.

Ramanujam et al. (1994), "Fluorescence Spectroscopy; A Diagnostic Tool for Cervical Intraepithelial Neoplasia (CIN)," *Gynecologic Oncology*, 52:31–38.

Reid et al. (1985), "Genital warts and cervical cancer. VII. An improved colposcopic index for differentiating benign papillomaviral infections from high–grade CIN," *Am. J. Obstet. Gynecol.*, 153(6):611–618.

Richards–Kortum et al. (1994), "Description and Performance of a Fiber–optic Confocal Fluorescence Spectrometer," *Applied Spectroscopy*, 48(3):350–355.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantitative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164–171.

Schmitt et al. (1994), "Confocal Microscopy in Turbid Media", *J. Opt. Soc. Am. A*, 11(8):2225–2235.

Schmitt et al. (1994), "Interferometric Versus Confocal Techniques for Imaging Microstructures in Turbid Biological Media", *Proc. SPIE*, 2135:1–12.

Schomacker et al. (1992), "Ultraviolet Laser–Induced Fluorescence of Colonic Polyps," *Gastroenterology*, 102:1155–1160.

Schomacker et al. (1992), "Ultraviolet Laser–Induced Fluorescence of Colonic Tissue; Basic Biology and Diagnostic Potential", *Lasers in Surgery and Medicine*, 12:63–78.

Schwartz (1993), "Real–time laser–scanning Confocal ratio imaging", *American Laboratory*, pp. 53–62.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Sheppard et al. (1978), "Depth of Field in the Scanning Microscope", *Optics Letters*, 3(3):115–117.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three–dimensional medical image sequences," *IEEE Transactions on Medial Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence,* 13(6):583–598.

Vincent et al. (1993), "Morphological grayscale reconstruction in image analysis: Applications and efficient algorithms," *IEEE Transactions on Image Processing,* 2(2):176–201.

Wang et al. (1999), "Fast algorithms for the estimation of motion vectors," *IEEE Transactions on Image Processing,* 8(3):435–438.

Weng et al. (1997), "Three–Dimensional Surface Reconstruction Using Optical Flow for Medical Imaging," *IEEE Transactions on Medical Imaging,* 16(5):630–641.

Wilson, "The Role of the Pinhold in Confocal Imaging Systems", *Confocal Microscopy Handbook,* Chapter 11, 113–126.

Wolberg et al. (1998) "Image morphing: a survey," *The Visual Computer,* 14:360–372.

You et al. (1996), "Behavioral analysis of anisotropic diffusion in image processing," *IEEE Transactions on Image Processing,* 5(11):1539–1553.

Zahm et al. (1998), "Colposcopic appearance of cervical intraepithelial neoplasia is age dependent," *Am. J. Obstet. Gynecol.,* 179(5):1298–1304.

Zeger et al. (1992), "Globally optimal vector quantizer design by stochastic relaxation," *IEEE Transactions on Signal Processing,* 40(2):310–322.

Zeng et al. (1993), "A computerized autofluorescence and diffuse reflectance spectroanalyser system for in vivo skin studies," *Phys. Med. Biol.,* 38:231–240.

Zeng et al. (1997), "Optimization of fast block motion estimation algorithms," *IEEE Transactions on Circuits and Systems for Video Technology,* 7(6):833–844.

Zhang et al. (1999), "Shape from shading: a survey," *IEEE Transactions on Pattern Analysis and Machine Intelligence,* 21(8):690–706.

Zheng et al. (1991), "Estimation of illumination direction, albedo, and shape from shading," *IEEE Transactions on Pattern Analysis and Machine Intelligence,* 13(7):680–702.

Zhengfang et al. (1998), "Identification of Colonic Dysplasia and Neoplasia by Diffuse Reflectance Spectroscopy and Pattern Recognition Techniques," *Applied Spectroscopy,* 52(6):833–839.

\* cited by examiner

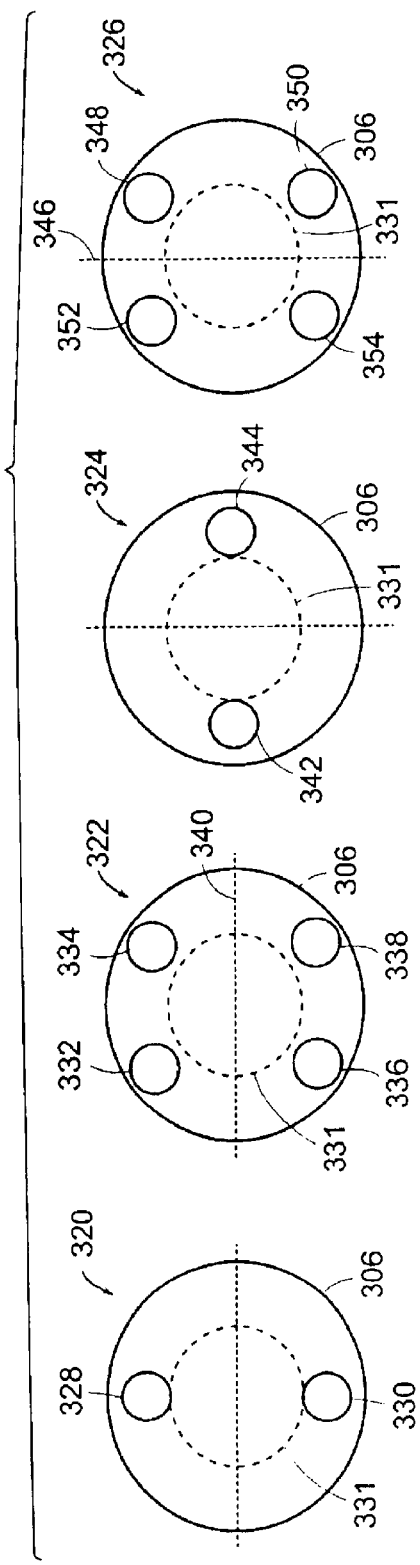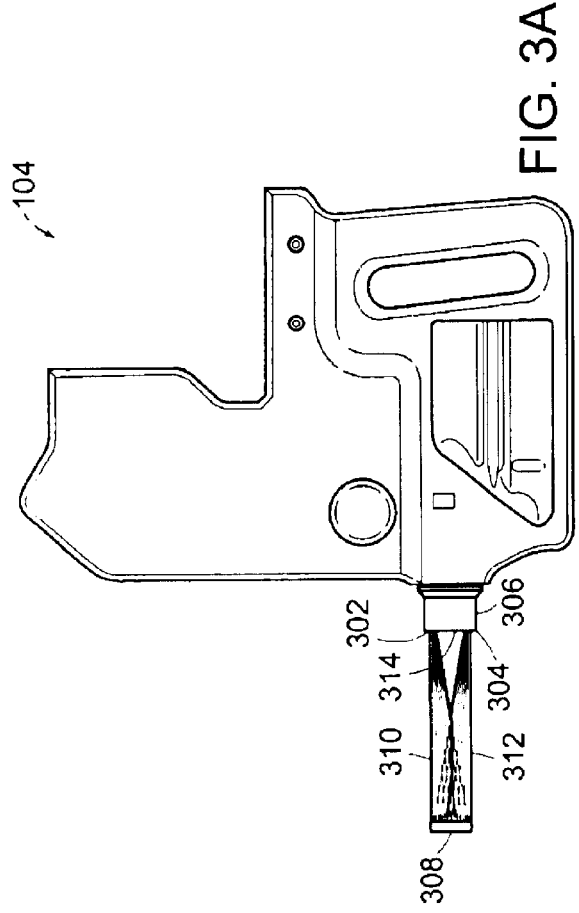
FIG. 3A
FIG. 3B

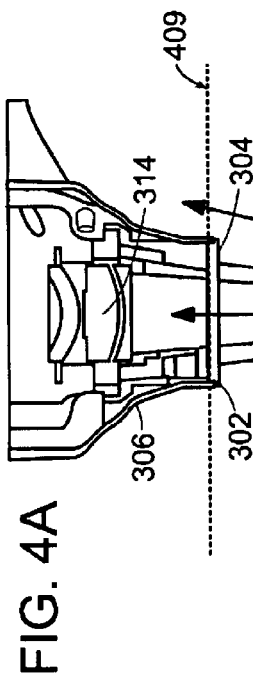
FIG. 4A
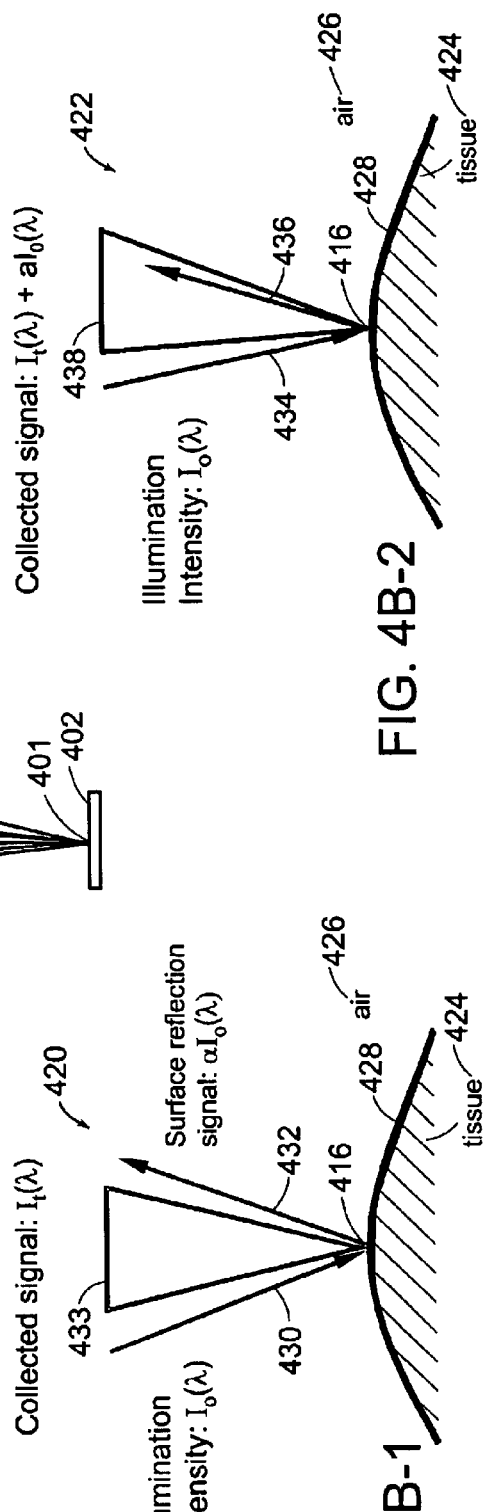
FIG. 4B-2
FIG. 4B-1

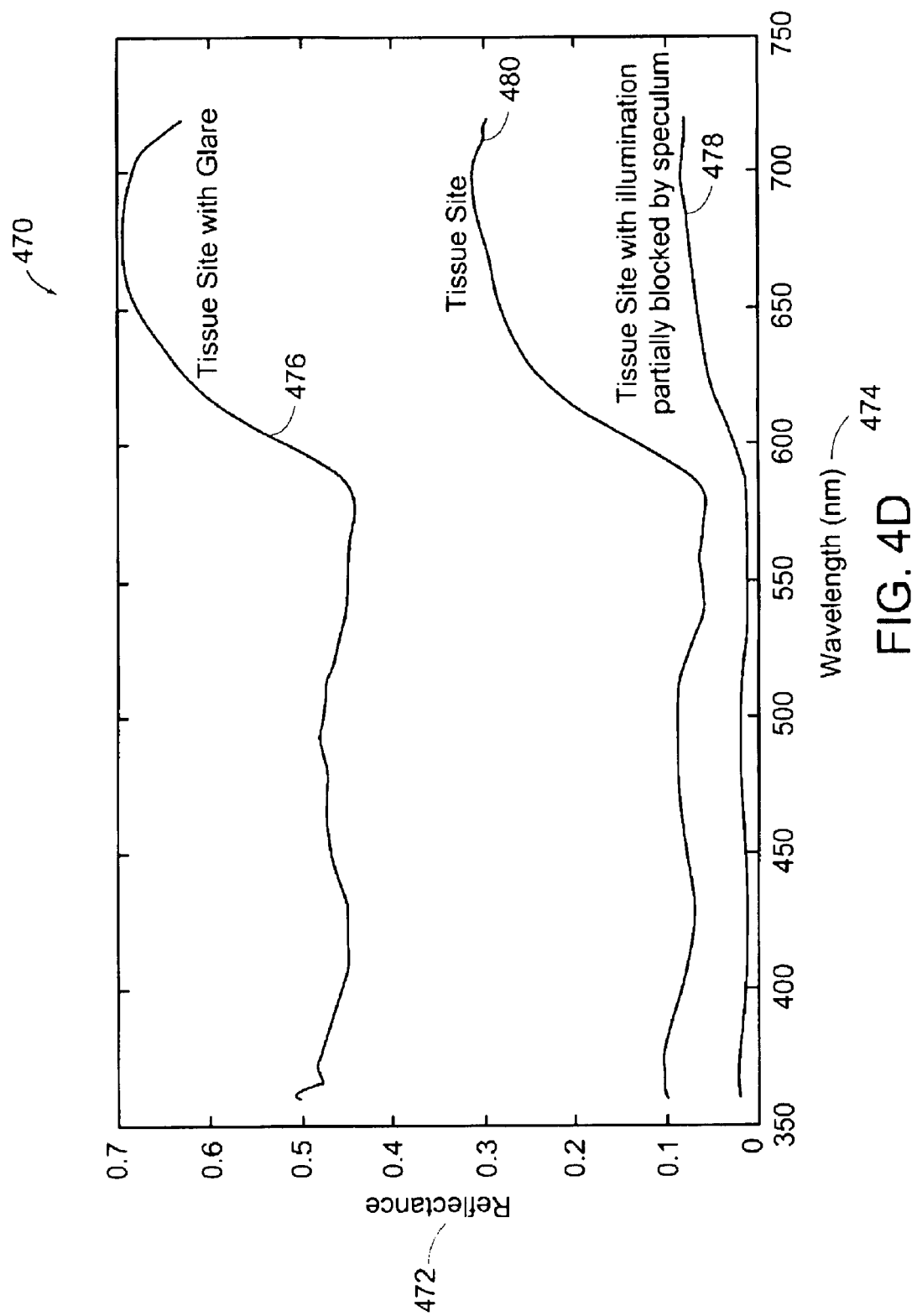

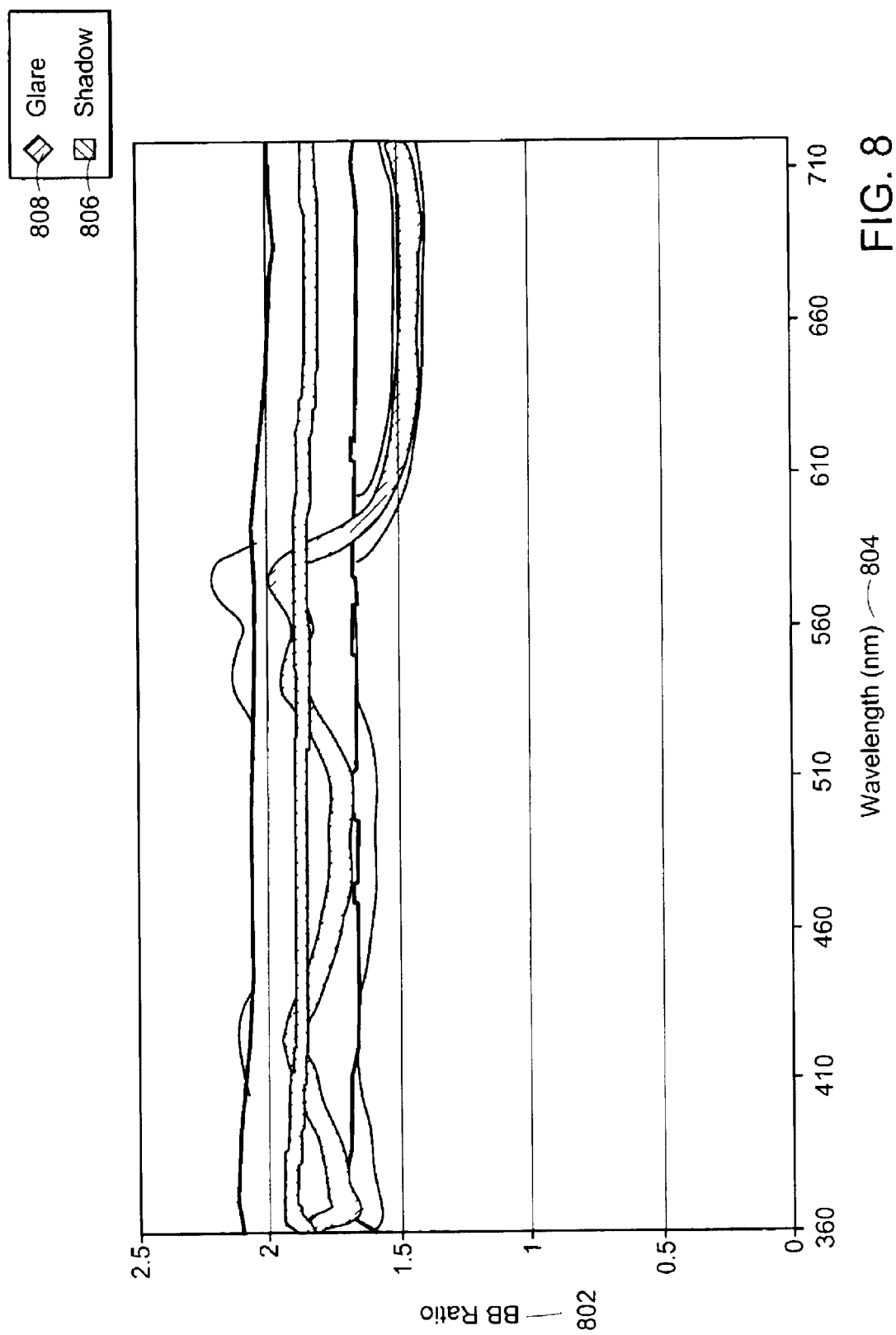

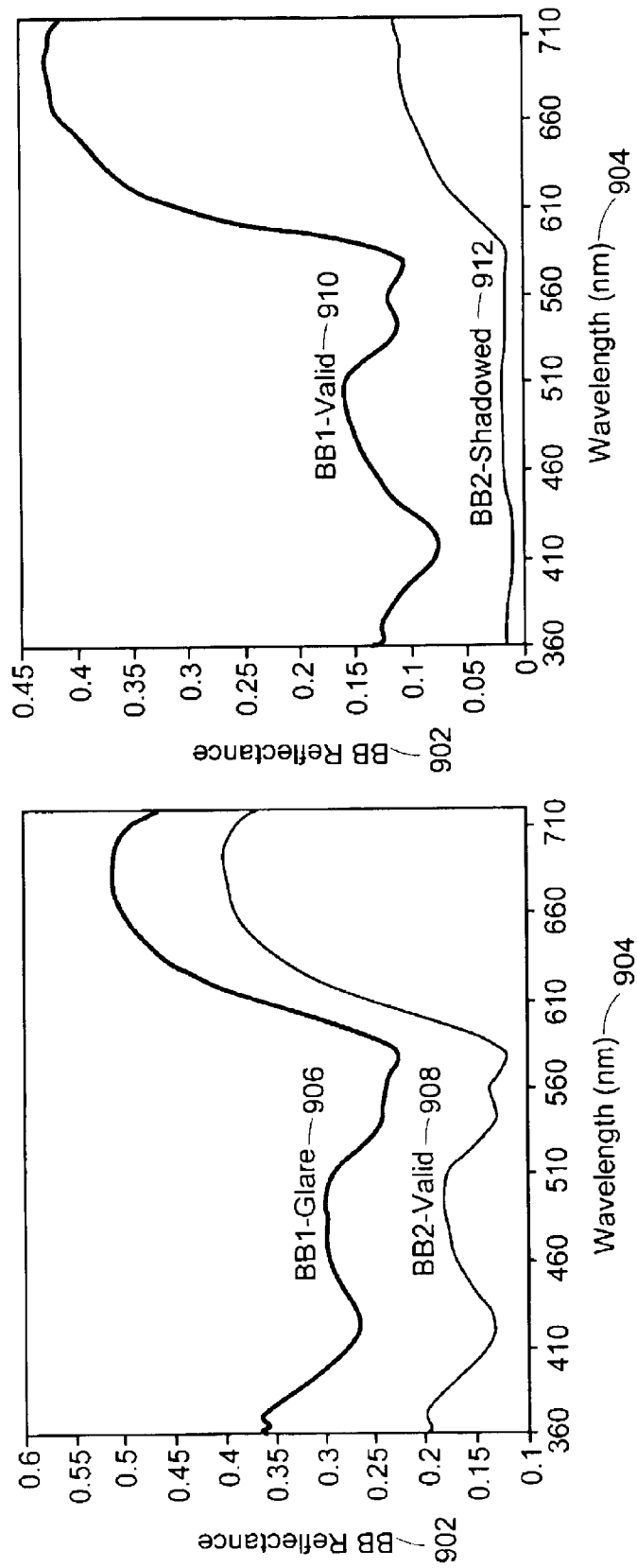

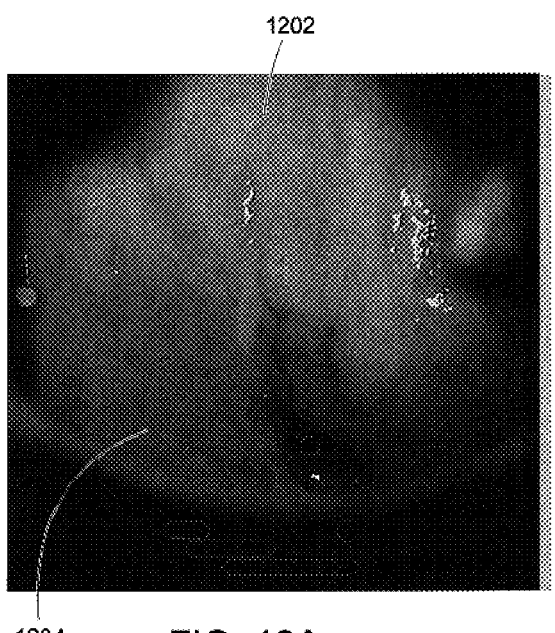
1204  FIG. 12A
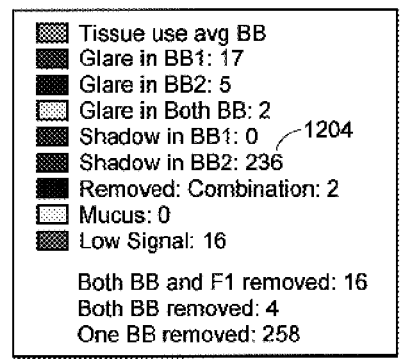
Tissue use avg BB
Glare in BB1: 17
Glare in BB2: 5
Glare in Both BB: 2
Shadow in BB1: 0   ⌐1204
Shadow in BB2: 236
Removed: Combination: 2
Mucus: 0
Low Signal: 16
Both BB and F1 removed: 16
Both BB removed: 4
One BB removed: 258
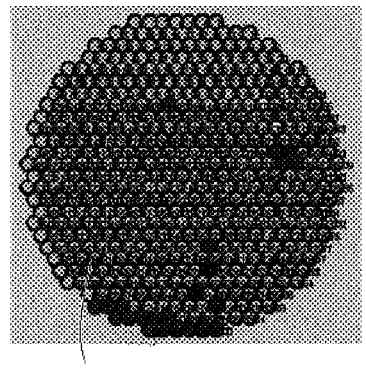
1204  FIG. 12B

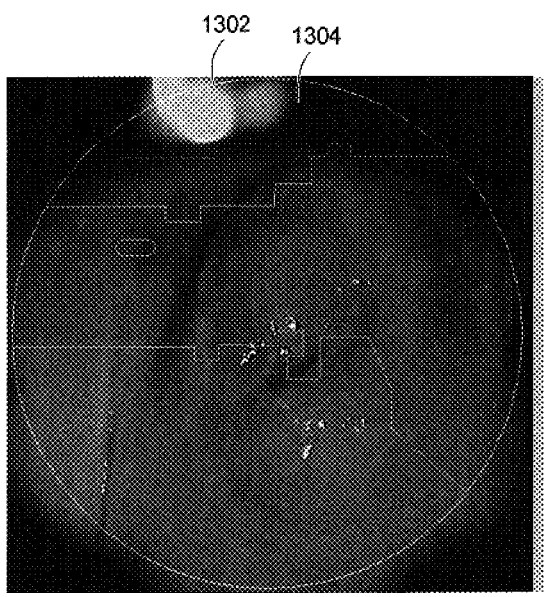
FIG. 13A
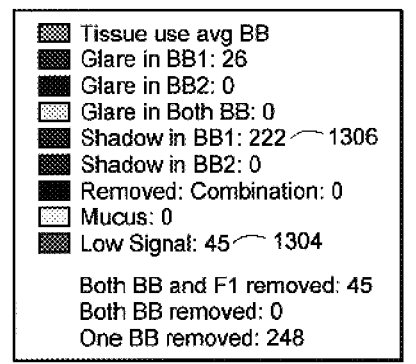
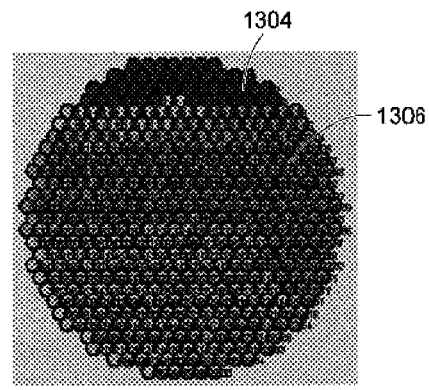
FIG. 13B

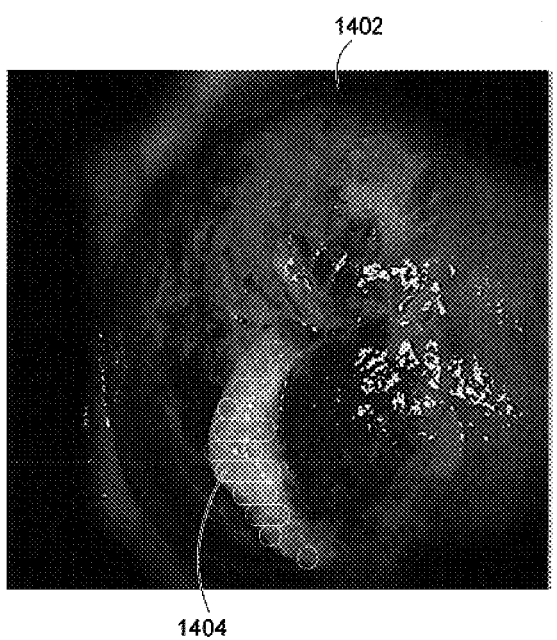
FIG. 14A
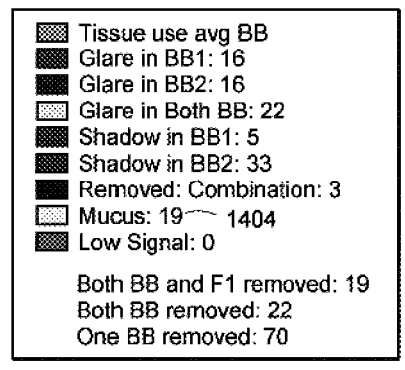
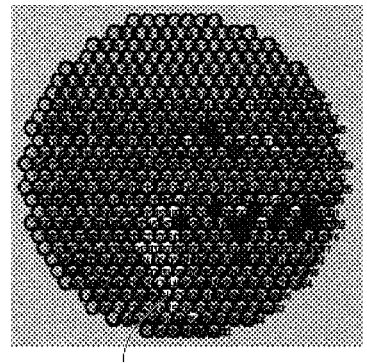
FIG. 14B

METHOD AND APPARATUS FOR IDENTIFYING SPECTRAL ARTIFACTS

PRIOR APPLICATIONS

This application claims the benefit of U.S. Provisional Patent Application Ser. No. 60/394,696, filed Jul. 9, 2002, the contents of which are hereby incorporated by reference.

FIELD OF THE INVENTION

This invention relates generally to spectroscopic methods. More particularly, in certain embodiments, the invention relates to an apparatus and methods for determining whether spectral data obtained from a region of a tissue sample are affected by one or more artifacts, such as glare, shadow, or an obstruction.

BACKGROUND OF THE INVENTION

Spectral analysis may be used to diagnose disease in tissue. For example, spectral data may be obtained during a diagnostic procedure in which spectral scans are performed on the tissue of a patient. One such diagnostic procedure is an acetowhitening procedure, in which a chemical agent is applied to tissue and the response of the tissue is captured in a spectral scan at some point following the application of the agent. The chemical agent is used, for example, to enhance the detected difference between spectral data obtained from normal tissue and spectral data obtained from abnormal or diseased tissue.

Spectral measurements of tissue may be non-representative of the actual condition of the tissue when they are affected by one or more artifacts. Artifacts include lighting artifacts such as glare or shadow, and obstructions, such as blood, a speculum, a smoke tube, or other instruments used during the procedure. Artifacts may be located and determined using visual evidence of a region of tissue at the time of the procedure. However, there are currently no other suitable methods of determining whether spectral data obtained from a region of a tissue sample are affected by an artifact. Also, current methods of obtaining spectral data do not allow for the characterization of tissue in the event an artifact adversely affects the data.

SUMMARY OF THE INVENTION

The invention provides an apparatus and methods for obtaining redundant spectral data in order to compensate for artifacts that may be present in optical sample analysis. By illuminating a region of tissue with light incident to the region at more than one angle, it is possible to obtain redundant spectral data for the region. If one set of data for a region is adversely affected by an artifact such as glare, shadow, or an obstruction, then redundant data for the region, obtained using light incident to the region at a different angle, may be useful. The redundant data may be used to describe the region of tissue, unobscured by the artifact.

The invention comprises methods for determining if spectral data obtained from a sample region are affected by an artifact, and if so, whether or not redundant data may be used in place of the affected data. Embodiments of the invention comprise the use of metrics to determine whether an artifact is affecting the spectral data from a region of a tissue sample. Methods also comprise determining what kind of artifact is affecting the data from the region. These metrics involve computations using values of the spectral data corresponding to a the region of the tissue sample. Methods of the invention do not rely on any additional visual evidence of the tissue sample, such as human visual inspection, to determine the presence or absence of an artifact. In certain embodiments, the presence of an artifact is desired. However, in preferred embodiments, the presence of an artifact is not desired, for example, because the artifact adversely affects the spectral data.

If it is determined that an artifact has rendered unusable a given set of data for a region of the sample, then the redundant data corresponding to the region may be considered. Since the redundant data is obtained using light incident to the region at a different angle from that used to obtain the affected data, the artifact may not have affected the redundant data. Multiple sets of redundant data may be used in order to compensate for one or more artifacts. Preferred methods of the invention comprise determining whether redundant data are affected by an artifact or, alternatively, whether redundant data are unaffected by the artifact and representative of the unobscured tissue. If the set of redundant data is representative of an unobscured tissue, such data may be used in place of the affected data in characterizing the region or determining the condition of the region of tissue. As mentioned above, more than one redundant set of data may be obtained. Also, if more than one set of data is determined to be unaffected by an artifact, averages of the unaffected data may be used to characterize the region of tissue.

Although specific metrics were developed for application to the analysis of in vivo cervical tissue subject to artifacts such as glare, shadow, and obstructions, methods for developing analogous metrics are also disclosed as part of the invention. Such methods may be used to create metrics for the analysis of other types of tissue such as in vivo or ex vivo colorectral, gastroesophageal, urinary bladder, lung, skin tissue, and/or any tissue comprising epithelial cells, for example. These methods may be used to create metrics for tissues that are subject to other states of health and/or other types of artifacts, in addition to those discussed herein. The invention also comprises methods of determining computational metrics for use in applications employing different types of spectral data than those specifically discussed herein.

In most embodiments discussed herein, spectral data are obtained as a function of wavelength within a range of between about 360 nm and 720 nm. However, in some embodiments, the range of wavelengths is from about 190 nm to about 1100 nm. In the methods discussed herein, where a range of about 360 nm to about 720 nm is specified, a broader range within about 190 nm and about 1100 nm is alternately used for some embodiments.

In one aspect, the invention is directed to a method of determining a condition of a region of a tissue sample using two or more sets of spectral data, each set obtained using light incident to the region at a unique angle. The method comprises the steps of: obtaining a first set of spectral data corresponding to a region of a tissue sample using light incident to the region at a first angle; obtaining a second set of spectral data corresponding to the region using light incident to the region at a second angle; selecting at least one of the two sets that is representative of the region of the tissue sample; and determining a condition of the region of the tissue sample based at least in part on a portion of the representative data.

Both the first and the second sets of spectral data comprise reflectance spectral data in some embodiments. In other embodiments, at least one of the two sets of spectral data comprises fluorescence spectral data. In some embodiments, the method further comprises obtaining one or more additional sets of spectral data corresponding to a region of interest, each set using light incident to the region at a unique angle.

The condition to be determined may be a state of health. In one embodiment the state of health comprises at least one of the following conditions: normal squamous tissue, metaplasia, Cervical Intraepithelial Neoplasia Grade I (CIN I), Cervical Intraepithelial Neoplasia Grade II (CIN II), Cervical Intraepithelial Neoplasia Grade III (CIN III), carcinoma in-situ (CIS), and cancer. In some embodiments, the state of health is a combination of two or more of the conditions above, such as Cervical Intraepithelial Neoplasia Grade II or Grade III (CIN II/III).

In another aspect, the invention is directed to a method of determining whether spectral data obtained from a region of a tissue sample are affected by an artifact. The method comprises the steps of: obtaining a first set of spectral data corresponding to a region of a tissue sample using light incident to the region at a first angle; obtaining a second set of spectral data corresponding to the region using light incident to the region at a second angle; and determining whether the first set of data is affected by an artifact based at least in part on a portion of the data from each of the two sets.

Both the first and the second sets of spectral data comprise reflectance spectral data in some embodiments. In other embodiments, the method comprises obtaining a third set of spectral data comprising fluorescence spectral data.

The invention comprises methods of applying various computational metrics in determining whether or not spectral data are affected by an artifact. According to one embodiment, the method of determining whether spectral data are affected by an artifact comprises computing a difference between $R_1$, a member of the first set of spectral data discussed above, and $R_2$, a member of the second set of spectral data discussed above, and comparing the difference to a constant, where $R_1$ and $R_2$ correspond to at least approximately identical wavelengths. This difference is a percent difference in some preferred embodiments.

In some preferred embodiments, the method of determining whether spectral data are affected by an artifact comprises computing N differences, $|R_1(X_i)-R_2(X_i)|$, optionally weighting each of the N differences using at least one of $R_1(X_i)$ and $R_2(X_i)$, defining a maximum of a subset of the N optionally-weighted differences, and comparing the maximum to a first constant, where i=1 to N, N is an integer, $X_i$ is a wavelength between about 360 nm and about 720 nm, $R_1(X_i)$ is a member of the first set of data corresponding to the wavelength $X_i$, and $R_2(X_i)$ is a member of the second set of data corresponding to the wavelength $X_i$.

The method of determining whether spectral data are affected by an artifact in some embodiments further comprises comparing $R_1(X_1)$ to a second constant, where $R_1(X_1)$ is a member of the first set of data corresponding to a wavelength $X_1$ between about 409 nm and about 429 nm.

The method of determining whether spectral data are affected by an artifact in some embodiments further comprises comparing the quotient $\{(R_1(X_1)/R_2(X_1))/(R_1(X_2)/R_2(X_2))\}$ to a second constant, where $X_1$ is a wavelength between about 360 nm and about 720 nm, $X_2$ is a wavelength between about 360 nm and about 720 nm, $R_1(X_1)$ is a member of the first set of data corresponding to the wavelength $X_1$, $R_2(X_1)$ is a member of the second set of data corresponding to the wavelength $X_1$, $R_1(X_2)$ is a member of the first set of data corresponding to the wavelength $X_2$, $R_2(X_2)$ is a member of the second set of data corresponding to the wavelength $X_2$. In one embodiment, $X_1$ is a wavelength between about 566 nm and about 586 nm, and $X_2$ is a wavelength between about 589 nm and about 609 nm. In one embodiments, the determining step further comprises comparing $R_1(X_3)$ to a third constant, where $R_1(X_3)$ is a member of the first set of data corresponding to a wavelength $X_3$ between about 689 and about 709 nm. In another embodiment, $X_3$ is between about 360 nm and about 720 nm. In yet another embodiment $X_3$ is between about 409 nm and about 429 nm.

The method of determining whether spectral data are affected by an artifact in some embodiments further comprises comparing a value Q to a second constant, where Q is an approximate slope of a plot of $\{R_1(X_i)/R_2(X_i)\}$ with respect to wavelength, over a subset of a wavelength range of about 360 nm to about 720 nm, $X_i$ is a wavelength between about 360 nm and about 720 nm, $R_1(X_i)$ is a member of the first set of data corresponding to the wavelength $X_i$, and $R_2(X_i)$ is a member of the second set of data corresponding to the wavelength $X_i$.

In another embodiment, the method of determining whether spectral data are affected by an artifact further comprises comparing $R_1(X_1)$ to a second constant and comparing $R_1(X_1)$ to $R_2(X_1)$, where $R_1(X_1)$ is a member of the first set of data corresponding to a wavelength $X_1$ between about 360 nm and about 720 nm, and $R_2(X_1)$ is a member of the second set of data corresponding to the wavelength $X_1$.

The method of determining whether spectral data are affected by an artifact in another embodiment further comprises comparing $R_1(X_1)$ to a second constant and comparing $R_1(X_1)$ to $R_2(X_1)$, where $R_1(X_1)$ is a member of the first set of data corresponding to a wavelength $X_1$ between about 489 nm and about 509 nm, and $R_2(X_1)$ is a member of the second set of data corresponding to the wavelength $X_1$.

According to some embodiments, the method of determining whether spectral data are affected by an artifact comprises comparing $R_1(X_1)$ to a constant, where $R_1(X_1)$ is a member of the first set of data corresponding to a wavelength $X_1$ between about 409 nm and about 429 nm. In one embodiment, the determining step further comprises comparing a value Q to a second constant, where the value Q is an approximate slope of a plot of $\{R_1(X_i)/R_2(X_i)\}$ with respect to wavelength, over a subset of a wavelength range of about 576 nm to about 599 nm, $X_i$ is a wavelength between about 360 nm and about 720 nm, $R_1(X_i)$ is a member of the first set of data corresponding to the wavelength $X_i$, and $R_2(X_i)$ is a member of the second set of data corresponding to the wavelength $X_i$.

In some embodiments, the method of determining whether spectral data are affected by an artifact comprises comparing the quotient $R_1(X_i)/R_1(X_2)$ to a constant, where $R_1(X_1)$ is a member of the first set of data corresponding to a wavelength $X_1$ between about 360 nm and about 720 nm, and $R_1(X_2)$ is a member of the first set of data corresponding to a wavelength $X_2$ between about 360 nm and about 720 nm. In one embodiment, $X_1$ is a wavelength between about 489 nm and 509 nm and $X_2$ is a wavelength between about 533 nm and about 553 nm.

According to one embodiment, the method of determining whether spectral data are affected by an artifact comprises comparing $R_1$ to a first constant and comparing $R_2$ to a second constant, where $R_1$ is a member of the first set of data corresponding to a wavelength between about 489 nm and about 509 nm and $R_2$ is a member of the second set of data corresponding to a wavelength between about 489 nm and about 509 nm.

The artifact comprises a lighting artifact in some embodiments. The lighting artifact comprises glare and/or shadow in some embodiments. In other embodiments, the artifact comprises an obstruction. An obstruction comprises blood, mucus, a speculum, and/or a smoke tube in these embodiment. There may be both lighting artifacts and obstruction artifacts in a given embodiment.

According to one embodiment, the tissue sample comprises cervical tissue. In some embodiments, the tissue sample contains epithelial cells as tissue components. The tissue sample comprises at least one of a group consisting of cervical, colorectal, gastroesophageal, urinary bladder, lung, and skin tissue in some embodiments.

In another aspect, the invention is directed to a method of determining whether spectral data corresponding to a region of a tissue sample is affected by an artifact using two sets of reflectance spectral data and one set of fluorescence spectral data. The method comprises the steps of: obtaining a first set of reflectance spectral data corresponding to a region of a tissue sample using light incident to the region at a first angle; obtaining a second set of reflectance spectral data corresponding to the region using light incident to the region at a second angle; obtaining a set of fluorescence spectral data corresponding to the region; and determining whether any of the data is affected by an artifact based at least in part on at least one of the following: a subset of the first set of reflectance spectral data, a subset of the second set of reflectance spectral data, and a subset of the set of fluorescence spectral data. In one embodiment, the determining step comprises comparing F to a constant, where F is a member of the set of fluorescence spectral data corresponding to a wavelength between about 469 nm and about 489 nm.

In another aspect, the invention is directed to methods of determining a spectral characteristic of an artifact. These include methods of determining computational metrics used to judge whether spectral data obtained from a region are affected by an artifact. A preferred method comprises the steps of: (a) at each of a first plurality of regions of tissue, obtaining a first set of reflectance spectral data known to be affected by a given artifact; (b) at each of a second plurality of regions of tissue, obtaining a second set of reflectance spectral data known not to be affected by the artifact; and (c) determining a spectral characteristic of the artifact based at least in part on the first and second sets of reflectance spectral data.

The method of determining a spectral characteristic in some embodiments comprises locating a wavelength at which there is a maximum difference between a mean of one or more members of the first set of reflectance spectral data corresponding to the wavelength and a mean of one or more members of the second set of reflectance spectral data corresponding to the wavelength, relative to a variation measure.

In some embodiments, the method of determining a spectral characteristic comprises computing N differences, $|\mu_i(A_j(X_i))-\mu_i(B_k(X_i))|$, and defining a maximum of a subset of the N differences, where i=1 to N, N is an integer, $X_i$ is a wavelength between about 360 nm and about 720 nm, j=1 to M1, M1 is an integer, $A_j(X_i)$ represents one of M1 members of the first set of reflectance spectral data corresponding to the wavelength $X_i$, k=1 to M2, M2 is an integer, $B_k(X_i)$ represents one of M2 members of the second set of reflectance spectral data corresponding to the wavelength $X_i$, $\mu_i(A_j(X_i))$ is a mean of the M1 members of the first set of data corresponding to the wavelength $X_i$, and $\mu(B_k(X_i))$ is a mean of the M2 members of the second set of data corresponding to the wavelength $X_i$.

According to some embodiments, the method of determining a spectral characteristic comprises computing N quotients, $[|\mu_i(A_j(X_i))-\mu_i(B_k(X_i))|/\{\sigma_i^2(A_j(X_i))+\sigma_i^2(B_k(X_i))\}^{0.5}]$, and defining a maximum of a subset of the N quotients, where i=1 to N, N is an integer, $X_i$ is a wavelength between about 360 nm and about 720 nm, j=1 to M1, M1 is an integer, $A_j(X_i)$ represents one of M1 members of the first set of reflectance spectral data corresponding to the wavelength $X_i$, k=1 to M2, M2 is an integer, $B_k(X_1)$ represents one of M2 members of the second set of reflectance spectral data corresponding to the wavelength $X_i$, $\mu_i(A_j(X_i))$ is a mean of said M1 members of the first set of data corresponding to the wavelength $X_i$, $\mu_i(B_k(X_i))$ is a mean of the M2 members of the second set of data corresponding to the wavelength $X_i$,$\sigma_i(A_j(X_i))$ represents a standard deviation of the M1 members of the first set of data corresponding to the wavelength $X_i$, and $\sigma_i(B_k(X_i))$ represents a standard deviation of the M2 members of the second set of data corresponding to the wavelength $X_i$.

The method of determining a spectral characteristic in some embodiments comprises computing N quotients, $[|\mu_i(A_j(X1_i)/A_j(X2_i))-\mu_i(B_k(X1_i)/B_k(X2_i))|/\{\sigma_i(A_j(X1_i)/A_j(X2i))+\sigma_i^2(B_k(X1_i)/B_k(X2_i))\}^{0.5}]$, and defining a maximum of a subset of the N quotients, where i=1 to N, N is an integer, X1, is a wavelength between about 360 nm and about 720 nm, X2, is a wavelength between about 360 nm and about 720 nm, j=1 to M1, M1 is an integer, $A_j(X_1,)$ represents one of M1 members of the first set of reflectance spectral data corresponding to the wavelength X1,, $A_j(X2_i)$ represents one of M1 members of the first set of reflectance spectral data corresponding to the wavelength $X2_i$, k=1 to M2, M2 is an integer, $B_k(X1_i)$ represents one of M2 members of the second set of reflectance spectral data corresponding to the wavelength $X1_i$, $B_k(X2_i)$ represents one of M2 members of the second set of reflectance spectral data corresponding to the wavelength $X2_i\mu_i(A_j(X1_i)/A_j(X2_i))$ is a mean of M1 quotients $A_j(X1_i)/A_j(X2_i)$ for j=1 to M1, $\mu_i(B_k(X1_i)/B_k(X2_i))$ is a mean of M2 quotients $B_k(X1_i)/B_k(X2_i)$ for k=1 to M2, $\sigma_i(A_j(X1_i)/A_j(X2_i))$ represents a standard deviation of the M1 quotients $A_j(X1_i)/A_j(X2_i)$, and $\sigma_i(B_k(X1_i)/B_k(X2_i))$ represents a standard deviation of the M2 quotients $B_k(X1_i)/B_k(X2_i)$.

In another aspect, the invention is directed to a method of determining a characteristic of a region of a tissue sample by obtaining at least two sets of reflectance spectral data, each using light incident to the region at a different angle, and eliminating data that is adversely affected by an artifact. The method comprises the steps of: (a) obtaining a first set of reflectance spectral data corresponding to a region of a tissue sample using light incident to the region at a first angle; (b) obtaining a second set of reflectance spectral data corresponding to the region using light incident to the region at a second angle; (c) determining whether at least one of the first set of reflectance data and the second set of reflectance data is affected by an artifact based at least in part on a subset of the first set of reflectance data and a subset of the second set of reflectance data; (d) rejecting at least one member of at least one of the first set of reflectance data and the second set of reflectance data determined in step (c) to be affected by the artifact; (e) determining a characteristic of the region of the tissue sample based at least in part on at least one member of at least one of the first set of reflectance data and the second set of reflectance data not rejected in step (d).

In some embodiments, the method further comprises obtaining a set of fluorescence spectral data corresponding to the region, and step (e) comprises determining the condition of the region of the tissue sample based at least in part on at least one member of at least one of the first set and the second set of reflectance data and at least one member of the set of fluorescence spectral data.

Although certain embodiments of the invention are specifically described with respect to fluorescence spectral data and/or reflectance (backscatter) spectral data, these methods may be adapted for use with other kinds of optical signal data that may be affected by artifacts, including Raman, infrared, video signal data, and combinations thereof.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. The patent or application file contains at least one drawing executed in color. Copies of this patent or patent application publication with color drawing(s) will be provided by the U.S. Patent and Trademark Office upon request and payment of the necessary fee.

FIG. 3A depicts a side view of a probe having top and bottom illumination sources according to an illustrative embodiment of the invention.

FIG. 3B depicts front views of four exemplary arrangements of illumination sources about a probe head according to an illustrative embodiment of the invention.

FIG. 4A depicts exemplary illumination of a region of a tissue sample using light incident to the region at two different angles according to an illustrative embodiment of the invention.

FIGS. 4B-1 and 4B-2 show schematic diagrams demonstrating specular and diffuse reflection from a region of a tissue sample according to an illustrative embodiment of the invention.

FIG. 4D shows a graph depicting exemplary values of reflectance spectral data as a function of wavelength for tissue regions affected by glare, tissue regions affected by shadow, and tissue regions affected by neither glare nor shadow according to an illustrative embodiment of the invention.

FIG. 8 shows a graph depicting as a function of wavelength mean values and confidence intervals of a ratio of BB1 and BB2 broadband reflectance spectral values for regions confirmed as being either glare-obscured or shadow-obscured tissue, according to an illustrative embodiment of the invention.

FIG. 9A shows a graph depicting BB1 and BB2 broadband reflectance spectral data for a region of tissue where the BB1 data is affected by glare but the BB2 data is not, according to an illustrative embodiment of the invention.

FIG. 9B shows a graph depicting BB1 and BB2 broadband reflectance spectral data for a region of tissue where the BB2 data is affected by shadow but the BB1 data is not, according to an illustrative embodiment of the invention.

FIG. 12A depicts an exemplary image of cervical tissue divided into regions for which two types of reflectance spectral data and one type of fluorescence spectral data are obtained, according to an illustrative embodiment of the invention.

FIG. 12B is a representation of the regions depicted in FIG. 1A and shows the categorization of each region according to an illustrative embodiment of the invention.

FIG. 13A depicts an exemplary image of cervical tissue divided into regions for which two types of reflectance spectral data and one type of fluorescence spectral data are obtained, according to an illustrative embodiment of the invention.

FIG. 13B is a representation of the regions depicted in FIG. 1A and shows the categorization of each region according to an illustrative embodiment of the invention.

FIG. 14A depicts an exemplary image of cervical tissue divided into regions for which two types of reflectance spectral data and one type of fluorescence spectral data are obtained.

FIG. 14B is a representation of the regions depicted in FIG. 11A and shows the categorization of each region according to an illustrative embodiment of the invention.

DESCRIPTION OF THE ILLUSTRATIVE EMBODIMENT

Figure 1:
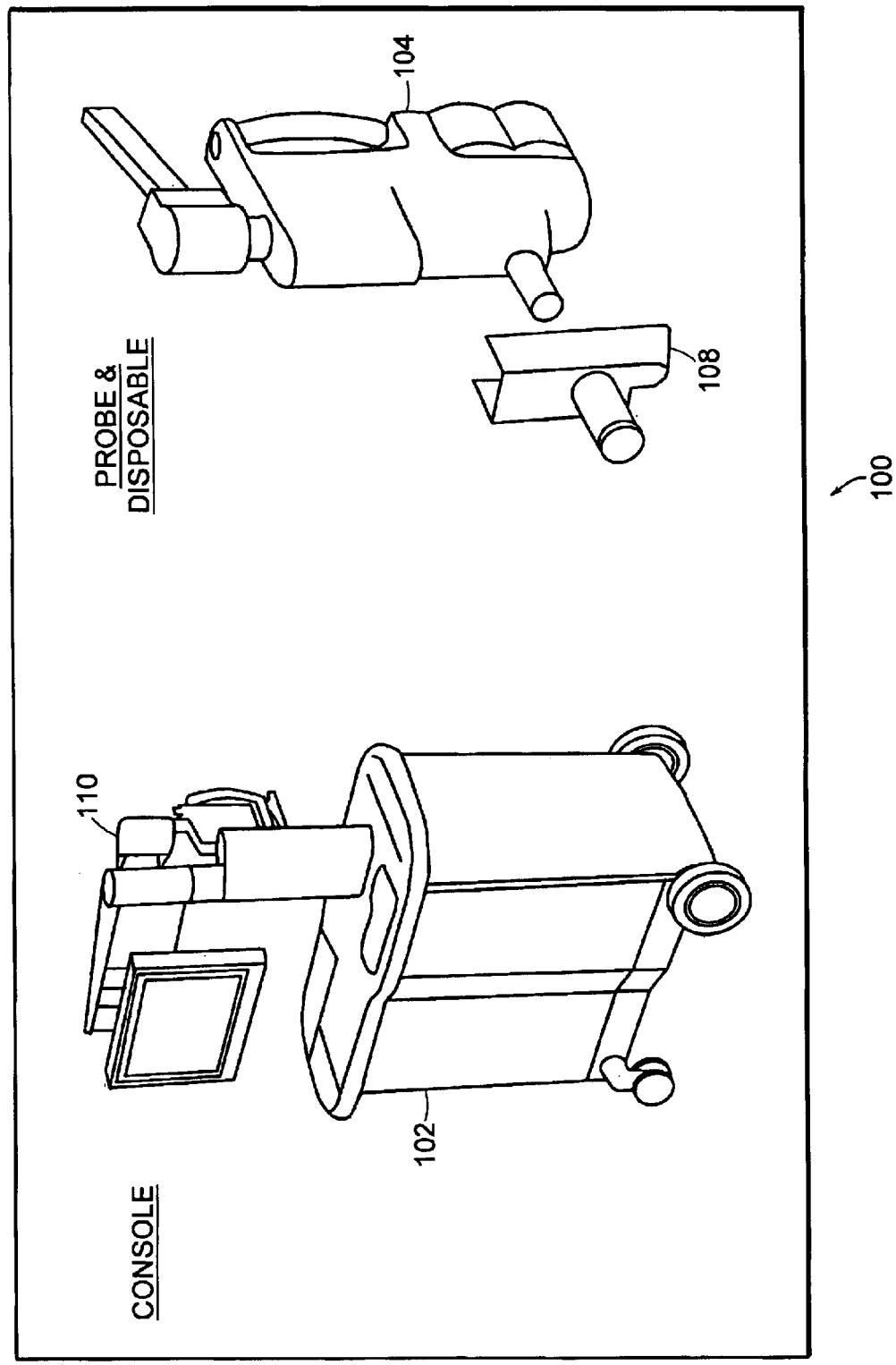
FIG. 1 depicts a spectroscopic system that employs a plurality of spectral types according to an illustrative embodiment of the invention.

In general, the invention relates to an apparatus and methods for determining whether spectral data obtained from a region of a tissue sample are affected by an artifact, such as glare, shadow, or an obstruction. The invention further relates to methods of using the known presence and absence of artifacts in reference sample regions to determine whether artifacts affect spectral data from test sample regions. An embodiment method of the invention comprises obtaining redundant spectral data of a given region of a sample, determining if the redundant spectral data are affected by an artifact, and if not, using the redundant data in place of artifact-affected data to determine a characteristic or condition of the region. The following is a detailed description of preferred embodiments of the invention.

Preferred methods utilize one or more types of spectral data such as fluorescence spectral data and reflectance spectral data to determine the condition of a tissue sample. Preferred methods of the invention comprise obtaining at least one redundant set of spectral data of a given type for a region of tissue. A redundant set is useful where one or more artifacts affect some but not all sets of the spectral data, such that the redundant set of data is unaffected by the artifact and is representative of the tissue. Preferred methods comprise using this representative data to determine a condition of a region of tissue. Methods of the invention also comprise determining whether an artifact exists by using data from at least two of the sets of spectral data obtained. Multiple redundant sets can be used to analyze multiple artifacts.

Methods of the invention generally apply to the analysis of a biological sample. For example, preferred methods comprise analyzing a region of cervical tissue during an acetowhitening test conducted on a patient. Other preferred methods comprise analyzing colorectal, gastroesophageal, urinary bladder, lung, skin tissue, and/or any tissue comprising epithelial cells. Some methods involve application of other agents in or on tissue; and some methods involve no application of agents to tissue.

One embodiment of the invention comprises obtaining spectral data of one or more types, such as reflectance spectral data and fluorescence spectral data, from a region of tissue in a biological sample. In this embodiment, at least two sets of spectral data are obtained from a given region of tissue, each set being obtained using light incident to the region at a different (average) angle. Then, the method comprises using at least a portion of the data from each of the two sets of data to determine whether either or both of the two sets of data are affected by an artifact. Artifacts include, among others, lighting artifacts, such as glare or shadow, and obstructions, such as blood, a speculum, a smoke tube, or other instruments used during the tissue examination procedure.

The invention further comprises an apparatus that provides illumination of a given region of a tissue sample using light incident to the region at more than one angle. This allows a user to obtain the multiple sets of spectral data described above. In one embodiment, the apparatus comprises a probe that has multiple illumination sources, variously located about a probe head. In an exemplary application, the angle of the cervix or other tissue being examined may be such that the light from one illumination source of the probe is specularly reflected toward the collection optics, causing glare. The spectral data obtained using this illumination source is therefore corrupted and is likely not representative of the region of tissue being examined. Similarly, if an object such as a speculum or other instrument blocks light from one illumination source, a shadow may be cast on the region of tissue, and the spectral data may therefore be corrupted and non-representative of the region. However, since the apparatus comprises more than one illumination source, spectral data obtained using light from one of the other illumination sources may not be affected by glare or shadow and may be usable in the analysis of the region of the sample.

Obstructions such as blood or mucus may affect spectral data obtained using an illumination source, and may result in data which is non-representative of the underlying region of tissue. Preferred methods of the invention include determining whether spectral data is affected by such an obstruction using the spectral data itself, without having to rely on other visual evidence of the tissue.

Additionally, the invention comprises methods of determining a spectral characteristic of an artifact using spectral data of regions of tissue affected by the artifact and spectral data of regions of tissue not affected by the artifact. These methods may be used, for example, to create metrics by which spectral data may be analyzed and determined to be either adversely affected by an artifact or properly representative of the region of tissue.

FIG. 1 depicts an exemplary spectroscopic system 100 employing a plurality of spectral data types according to an illustrative embodiment of the invention. The spectroscopic system of FIG. 1 comprises a console 102 connected to a probe 104 by means of a cable 106. The cable 106 carries electrical and optical signals between the console 102 and the probe 104. The probe 104 accommodates a disposable component 108 which may be used once and discarded. The console 102 and the probe 104 are mechanically connected by an articulating arm 110, which can also support the cable 106. The console 102 contains much of the hardware and the software of the system, and the probe 104 contains the necessary hardware for making suitable spectroscopic observations. The details of the system are further explained in conjunction with FIG. 2.

Figure 2:
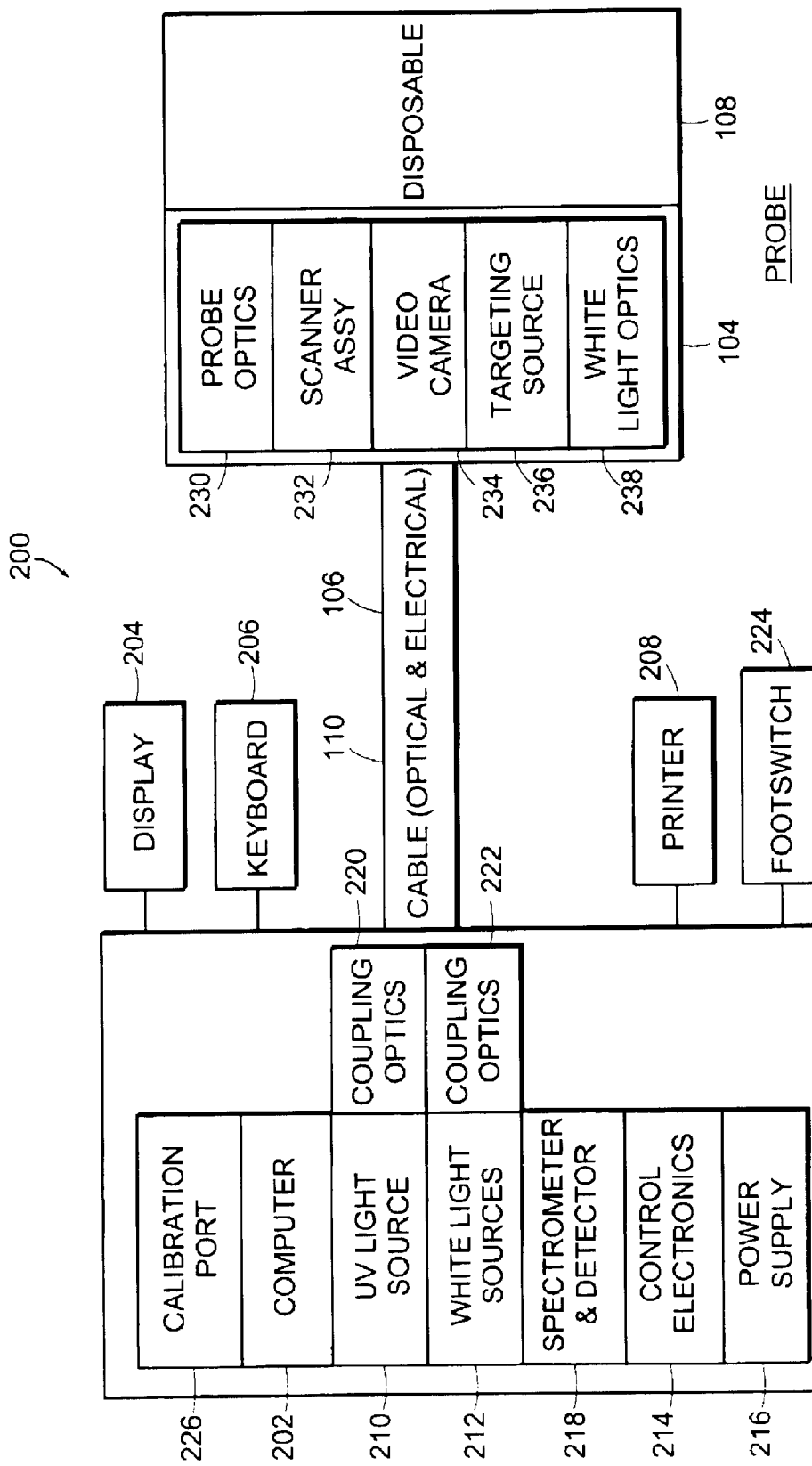
FIG. 2 depicts a block diagram of the spectroscopic system of FIG. 1 according to an illustrative embodiment of the invention.

FIG. 2 shows an exemplary operational block diagram 200 of a spectroscopic system of the type depicted in FIG. 1. According to an illustrative embodiment, the spectroscopic system of FIG. 1 and FIG. 2 is substantially the same as single-beam spectrometer devices, but is adapted to include the features of the invention. In other embodiments, the spectroscopic system of FIG. 1 and FIG. 2 is substantially the same as double-beam spectrometer devices, adapted to include the features of the invention. Still other embodiments use other types of spectroscopic systems. The console 102 comprises a computer 202 which executes software that controls the operation of the spectroscopic system 100. The software comprises one or more modules recorded on machine-readable media such as magnetic disks, magnetic tape, CD-ROM, and semiconductor memory, for example. Preferably, the machine-readable medium is resident within the computer 202. In alternative embodiments, the machine-readable medium can be connected to the computer 202 by a communication link. In alternative embodiments, one can substitute computer instructions in the form of hardwired logic for software, or one can substitute firmware (i.e., computer instructions recorded on devices such as PROMs, EPROMS oe EEPROMs, or the like) for software. The term machine-readable instructions as used herein is intended to encompass software, hardwired logic, firmware and the like.

The computer 202 in FIG. 2 is a general purpose computer. The computer 202 can be an embedded computer, a personal computer such as a laptop or desktop computer, of other type of computer, that is capable of running the software, issuing suitable control commands, and recording information in real time. In one embodiment, the computer 202 has a display 204 for reporting information to an operator of the spectroscopic system 100, a keyboard 206 for enabling the operator to enter information and commands, and a printer 208 for providing a print-out, or permanent record, of measurements made by the spectroscopic system 100 and for printing diagnostic results, for example, for inclusion in the chart of a patient. In an illustrative embodiment of the invention, some commands entered at the keyboard enable a user to select a particular spectrum for analysis or to reject a spectrum, and to select particular segments of a spectrum for normalization. Other commands enable a user to select the wavelength range for each particular segment and to specify both wavelength contiguous and non-contiguous segments.

The console 102 in the embodiment shown in FIG. 2 also comprises an ultraviolet (UV) source 210 such as a nitrogen laser or a frequency-tripled Nd:YAG laser, one or more white light sources 212 such as one, two, three, four, or more Xenon flash lamps, and control electronics 214 for controlling the light sources both as to intensity and as to the time of onset of operation and the duration of operation. One or more power supplies 216 are included in the console 102 in this embodiment to provide regulated power for the operation of all of the components. In this embodiment, the console 102 of FIG. 2 also comprises at least one spectrometer and at least one detector (spectrometer and detector 218) suitable for use with each of the light sources. In some embodiments, a single spectrometer can operate with both the UV light source and the white light source. In some embodiments, the same detector can record UV and white light signals, and in some embodiments different detectors are used for each light source.

The console 102 in the embodiment shown in FIG. 2 also comprises coupling optics 220 to couple the UV illumination from the UV light source 210 to one or more optical fibers in the cable 106 for transmission to the probe 104, and coupling optics 222 for coupling the white light illumination from the white light sources 212 to one or more optical fibers in the cable 106 for transmission to the probe 104. The spectral response of a specimen to UV illumination from the UV light source 210 observed by the probe 104 is carried by one or more optical fibers in the cable 106 for transmission to the spectrometer and detector 218 in the console 102. The spectral response of a specimen to the white light illumination from the white light source 212 observed by the probe 104 is carried by one or more optical fibers in the cable 106 for transmission to the spectrometer and detector 218 in the console 102. In the embodiment shown in FIG. 2, the console 102 comprises a footswitch 224 to enable an operator of the spectroscopic system 100 to signal when it is appropriate to commence a spectral observation by stepping on the switch. In this manner, the operator has his or her hands free to perform other tasks, for example, aligning the probe 104.

The console 102 of FIG. 2 comprises a calibration port 226 for calibrating the optical components of the spectrometer system. In an embodiment, an operator places the probe 104 in registry with the calibration port 226 and issues a command that starts the calibration operation. In one embodiment of the calibration operation, a calibrated light source provides a calibration signal in the form of illumination of known intensity over a range of wavelengths, and/or at a number of discrete wavelengths. The probe 104 detects the calibration signal. The probe 104 transmits the detected signal through the optical fiber in the cable 106 to the spectrometer and detector 218. A test spectral result is obtained. A calibration of the spectral system is computed as the ratio of the amplitude of the known illumination at a particular wavelength divided by the test spectral result at the same wavelength. In an embodiment, calibration is performed before use of the probe 104 on a patient. Here, calibration would account for patient-to-patient variation.

In an embodiment, the probe 104 comprises probe optics 230 for illuminating a specimen to be analyzed with UV light from the UV source 210 and for collecting the fluorescent and reflectance (backscatter) illumination from the specimen that is being analyzed. The probe 104 in the embodiment shown in FIGS. 1 and 2 comprises a scanner assembly 232 that provides illumination from the UV source 210, for example, in a raster pattern over a target area of the specimen of cervical tissue to be analyzed. The probe 104 comprises a video camera 234 for observing and recording visual images of the specimen under analysis. The probe 104 comprises a targeting souce 236, which can be used to determine where on the surface of the specimen to be analyzed the probe 104 is pointing. The probe 104 also comprises white light optics 238 to deliver white light from white light sources 212 for recording the reflectance data and to assist the operator in visualizing the specimen to be analyzed. In an embodiment, once the operator aligns the spectroscopic system and depresses the footswitch 224, the computer 202 controls the actions of the light sources 210, 212, the coupling optics 220, 222, the transmission of light signals and electrical signals through the cable 106, the operation of the probe optics 230 and the scanner assembly 232, the retrieval of observed spectra, the coupling of the observed spectra into the spectrometer and detector 218 via the cable 106, the operation of the spectrometer and detector 218, and the subsequent signal processing and analysis of the recorded spectra.

FIG. 3A depicts a side view of a probe 104 having top and bottom illumination sources 302, 304 according to an illustrative embodiment of the invention. In this embodiment, the illumination sources 302, 304 are situated at an upper and a lower location about the perimeter of a probe head 306 such that at any region on the surface of a tissue sample 308 there is illuminating light incident to the region at each of two different angles. Here, the illuminating light is depicted by the upper and lower intersecting cones 310, 312. The probe head 306 contains probe optics 230 for illuminating regions of tissue and for collecting illumination reflected or otherwise emitted from regions of tissue. In this embodiment, probe optics for collecting illumination 314 are located between the top and bottom illumination sources 302, 304. In some embodiments, other arrangements of illuminating and collecting probe optics 230 which allow the illumination of a given region of tissue with light incident to the region at more than one angle are used. One such arrangement includes collecting optics 314 positioned around illuminating optics.

In one embodiment, the top and bottom illumination sources 302, 304 are alternately turned on and off in order to sequentially illuminate the tissue at equal and opposite angles relative to the collection axis. For example, the top illumination source 302 is turned on while the bottom illumination source 304 is turned off, such that spectral measurements may be obtained for light reflected from a region of the tissue sample 308 illuminated with light incident to the region at a first angle. This angle is relative to the surface of the tissue sample at a point on the region, for example. Then, the top illumination source 302 is turned off while the bottom illumination source 304 is turned on, such that spectral measurements may be obtained using light incident to the region at a second angle. If data obtained using one of the illumination sources is adversely affected by an artifact, such as glare or shadow, then data obtained using another illumination source, with light incident to the region at a different angle, may be unaffected by the artifact and may still be useful.

In some embodiments, the spectral measurements include reflectance data obtained over a range of wavelengths. In some embodiments, the spectral measurements include fluorescence data obtained over a range of wavelengths.

Embodiment methods include different illumination alternation schemes. For example, the top and the bottom illumination sources 302, 304 may be alternately cycled on and off more than once while obtaining data for a given region. Also, the illumination sources may overlap, such that more than one illumination source is on at one time for at least part of the illumination collection procedure. Other illumination alternation schemes are possible, depending at least in part on the arrangement of illumination sources in relation to the probe head 306.

After data are obtained from one region of the tissue using light incident to the region at more than one angle, data may likewise be obtained from another region of the tissue. An embodiment method comprises illuminating a target area of the tissue sample region-by-region using a scanner assembly 232. An embodiment comprises alternately illuminating a first region using light incident to the region at more than one angle as described above, then adjusting the probe optics 230 to repeat the illumination sequence at a different region within the target area of the tissue sample. In an embodiment, the process is repeated until a desired subset of the entire target area has been scanned. In one embodiment, five hundred regions are scanned within a target area having a diameter of about 25-mm. In an embodiment, the scan of the aforementioned five hundred regions takes about 12 seconds. In other embodiments, the number of regions scanned, the size of the target area, and/or the duration of the scan vary from the above.

FIG. 3B depicts front views of four exemplary arrangements 320, 322, 324, 326 of illumination sources about a probe head 306 according to an illustrative embodiment of the invention. The drawings are not to scale; they simply serve to illustrate exemplary relative arrangements of illumination sources about the perimeter of a probe head 306. Other embodiment arrangements include collecting optics 314 positioned around the perimeter of the probe head 306. The first arrangement 320 of FIG. 3B has one top illumination source 328 and one bottom illumination source 330, which are alternately cycled on and off as described above. The illumination sources are arranged about the collecting optics 331, which are located in the center of the probe head 306. Light from an illumination source is reflected from the tissue and captured by the collecting optics 331.

The second arrangement 322 of FIG. 3B is similar to the first arrangement 320, except that there are two illumination sources 332, 334 in the top half of the probe head 306 and two illumination sources 336, 338 in the bottom half of the probe head 306. In one embodiment, the two lights above the midline 340 are turned on and the two lights below the midline 340 are turned off while obtaining a first set of spectral data; then the lights above the midline 340 are turned off and the lights below the midline 340 are turned on while obtaining a second set of spectral data. An alternate embodiment comprises turning only one of the four illumination sources on at a time to obtain four sets of spectral data for a given region. Another embodiment comprises turning the illumination sources on and off in various other patterns. Some embodiments comprise using noncircular or otherwise differently shaped illumination sources, and/or using a different number of illumination sources. Some embodiments comprise using arrangements where the collecting optics are positioned about the illuminating optics. Some embodiments comprise arrangements where the collecting optics are otherwise positioned with respect to the illuminating optics.

The third arrangement 324 of FIG. 3B includes each illumination source 342, 344 positioned on either side of the probe head 306. An embodiment comprises alternating these lights in a manner analogous to those described for the first arrangement 320.

The fourth arrangement 326 of FIG. 3B is similar to the second arrangement 322, except that the lights 348, 350 on the right side of the probe head 306 are turned off and on together, alternately with lights 352, 354 on the left side of the probe head 306. Thus, two sets of spectral data may be obtained for a given region, one set using lights on the right of the midline 346, and the other set using lights on the left of the midline 346.

FIG. 4A depicts exemplary illumination of a region 401 of a tissue sample 402 using light incident to the region 401 at two different angles 406, 410 according to an illustrative embodiment of the invention. FIG. 4A demonstrates that source light position may affect whether or not data is affected by glare. Note the probe head 306 of FIG. 4A has been rotated from its position depicted in FIG. 3A for illustrative purposes. In an embodiment, the top illumination source 302 and bottom illumination source 304 are turned on sequentially and illuminate the surface of a tissue sample 402 at equal and opposite angles relative to the collection axis 409. Arrows represent the light 406 emitted from the top illumination source 302, and the light 408 specularly reflected from the surface of the region 401 of the tissue sample 402. In preferred embodiments, it is desired to collect diffusely reflected light, as opposed to specularly reflected light 408 (glare). Since the specularly reflected light 408 from the top illumination source 302 does not enter the collecting optics 314 in the example illustrated in FIG. 4A, a set of data obtained using the top illumination source 302 would not be affected by glare.

However, in the example illustrated in FIG. 4A, the emitted light 410 from the bottom illumination source 304 reaches the surface of the region 401 of the tissue 402 and is specularly reflected into the collecting optics 314, shown by the arrow 412. Data obtained using the bottom illumination source 304 in the example pictured in FIG. 4A would be affected by glare. This data may not be useful, for example, in determining a characteristic or a condition of the region 401 of the tissue 402. In this example, it would be advantageous to instead use the set of data obtained using the top illumination source 302 since it is not affected by glare.

FIGS. 4B-1 and 4B-2 show schematic diagrams demonstrating specular and diffuse reflection from a region 416 of a tissue sample 424 according to an illustrative embodiment of the invention. FIGS. 4B-1 and 4B-2 demonstrate that position of the collection optics may affect whether or not data is affected by glare. The diagram 420 of FIG. 4B-1 demonstrates the specular reflection of light incident 430 to the surface 428 of a region 416 of tissue 424 with collection optics centered to provide an acceptance cone 433 as shown. This is analogous to the reflection of light from the top illumination source 302 illustrated in FIG. 4A. There is an interface 428 between the tissue 424 and the surrounding air 426. Light 430 with illumination intensity $I_o(\lambda)$ strikes the air-tissue interface 428 at the region 416. Light 432 with a fraction of the initial illumination intensity, $\alpha I_o(\lambda)$, is specularly reflected from the surface 428, where $\alpha$ is a real number between 0 and 1. The acceptance cone 433 is the space through which light is diffusely reflected from the tissue 424 into the collecting optics 314, in this embodiment. In other embodiments, light may also be emitted or otherwise transmitted from the surface of the tissue. In the embodiment illustrated in FIG. 4B-1, it is the diffusely reflected light that is of interest, since spectral data obtained from diffusely reflected light can be used to determine the condition of the region of the sample. Since there is no specular reflection within the acceptance cone 433, only diffusely reflected light is collected, and the collected signal corresponds to $I_r(\lambda)$, where $I_r(\lambda)$ is the intensity of light diffusely reflected from the region 416 on the surface 428 of the tissue 424.

The diagram 422 of FIG. 4B-2 demonstrates the specular reflection of light incident to the surface 428 of a region 416 of tissue 424 with collection optics off-center, providing an acceptance cone 438 as shown. In the diagram 422 of FIG. 4B-2, light 434 with illumination intensity $I_o(\lambda)$ strikes the surface 428 of the tissue 424. Light 436 with a fraction of the initial illumination intensity, $\alpha I_o(\lambda)$, is specularly reflected from the surface 428, where $\alpha$ is a real number between 0 and 1. Unlike in the diagram 420 of FIG. 4B-1, there is specular reflection within the acceptance cone 438 in the diagram 422 of FIG. 4B-2, and so both diffusely reflected light and specularly reflected light reach the collecting optics 314. Thus, in the example illustrated in diagram 422, the collected signal corresponds to an intensity represented by the sum $I_r(\lambda)+\alpha I_o(\lambda)$. It may be difficult or impossible to separate the two components of the measured intensity, thus, the data may not be helpful in determining the condition of the region 416 of the tissue sample 424, due to the glare effect.

Figure 4C:
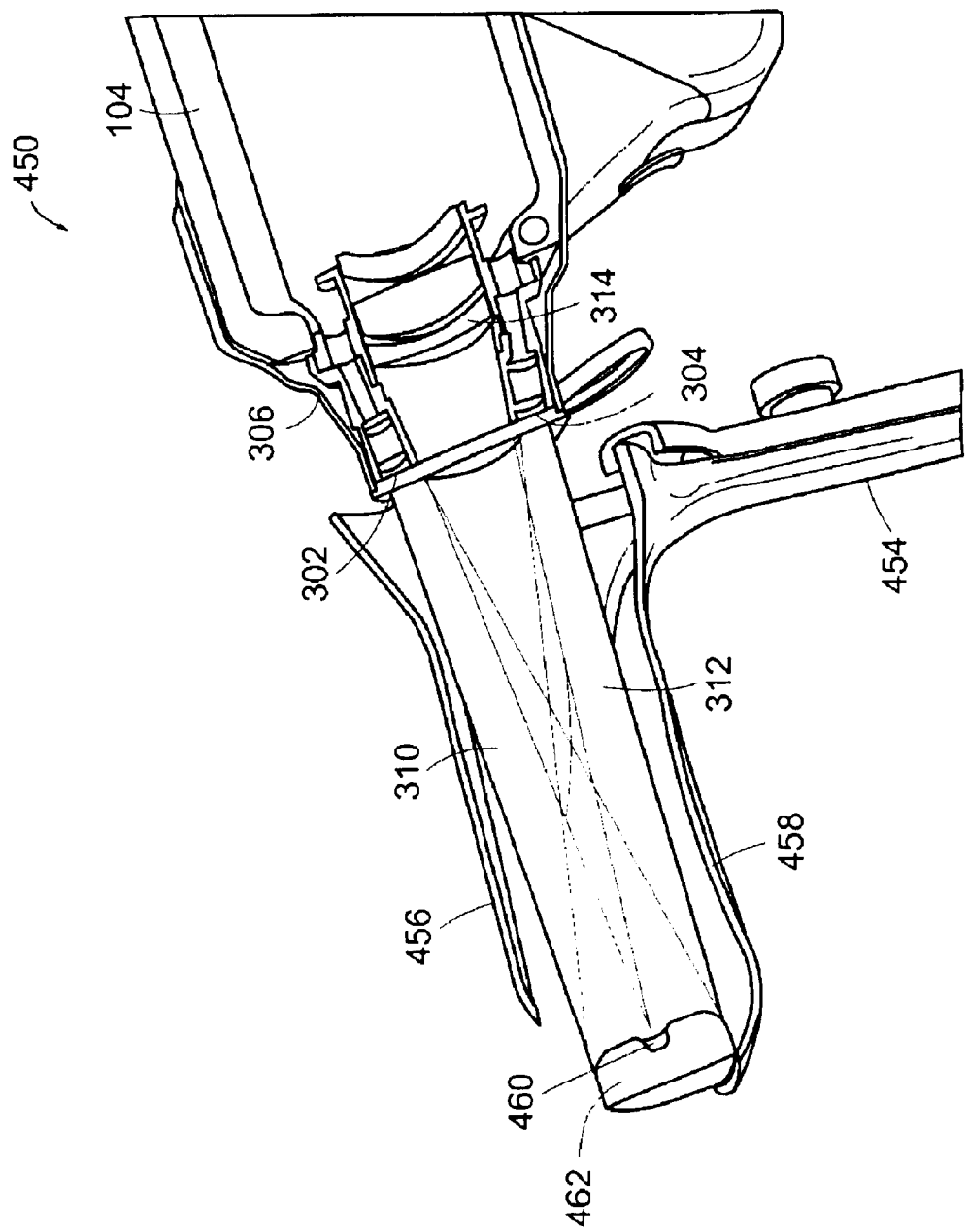
FIG. 4C depicts illumination of a cervical tissue sample using a probe and a speculum according to an illustrative embodiment of the invention.

FIG. 4C is a diagram 450 depicting illumination of a region 460 of a cervical tissue sample 462 using a probe 104 and a vaginal speculum 454 according to an illustrative embodiment of the invention. Probe optics for collecting illumination 314 are located between the top and bottom illumination sources 302, 304. In a preferred embodiment, the probe 104 operates without physically contacting the tissue being analyzed. In one embodiment, a disposable sheath is used to cover the probe head 306, for example, in case of incidental contact of the probe head 306 with the patient's body. In an embodiment, the sheath is disposed of after a single use on a patient. In an embodiment, the disposable sheath has a unique identifier, such as a two-dimensional bar code. The apparatus and methods described herein are not limited to use in the analysis of vaginal tissue. Other tissue types may be analyzed using these methods, including colorectal, gastroesophageal, urinary bladder, lung, skin tissue, and/or any tissue comprising epithelial cells, for example.

The diagram 450 of FIG. 4C demonstrates that a misalignment of the probe 104 may create conditions where either or both of the top and bottom speculum blades 456, 458 block part or all of the illumination path from either or both of the intersecting upper and lower cones of illuminating light 310, 312, thereby affecting the spectral data obtained for the region 460 of the tissue sample 462. The speculum blades, or other obstructions such as a smoke tube or other implements used during examination, may physically obstruct the region 460 being analyzed, or may partially obstruct the light illuminating the region 460 causing a shadow. In either case, the spectral data obtained may be adversely affected and rendered unusable for characterizing the region of the tissue sample. Obtaining multiple sets of spectral data using illumination from sources at various positions and angles improves the chances of obtaining at least one set of spectral data that is not affected by glare, shadow, and/or obstructions.

FIG. 4D shows a graph 470 depicting exemplary values of reflectance spectral data 472 as a function of wavelength 474 for tissue regions affected by glare 476, tissue regions affected by shadow 478, and tissue regions affected by neither glare nor shadow 480 according to an illustrative embodiment of the invention. The reflectance spectral data 472 represent the fraction of incident light that is reflected from the sample. The intensity of the incident light may be determined using a NIST-traceable diffuse reflectance target, such as a 10% diffuse reflectance target. The graph 470 shows that the reflectance values of a region of tissue affected by glare 476 are higher at all measured wavelengths than the reflectance of a region of tissue not affected by glare 480. The graph 470 also shows that the reflectance values of a region of tissue with illumination partially blocked by a speculum blade such that the region is in shadow, are lower at all measured wavelengths than the reflectance of a region of tissue not affected by shadow 480. The shapes of all three curves 476, 478, 480 are different. In this example, the data affected by glare or shadow may not be usable to determine a condition or characteristic of the region of the sample, if the data are not representative of the region of the tissue sample. There is no simple way to accurately separate out the effect of the glare or shadow in order to determine the diffuse reflection at the region of the tissue, in this case. Hence, glare and shadow may adversely affect spectral data obtained for a region of a tissue sample.

An illustrative embodiment of the invention comprises obtaining one fluorescence spectrum and two broadband reflectance spectra at each of a plurality of scan locations of the sample tissue. Here, a spectrum refers to a collection of spectral data over a range of wavelengths. In one embodiment method, spectral data are collected over a range of wavelengths between 360 and 720 nm in 1 nm increments. In other embodiments, the range of wavelengths is between about 190 nm and 1100 nm. Here, the two reflectance spectra are referred to as the BB1 (broadband one) and BB2 (broadband two) spectra. BB1 and BB2 differ in the way that the tissue is illuminated at the time the spectral data are obtained as described below. In one embodiment, the probe head 306 has 4 illumination sources located circumferentially about the collection optics. Two sources are above and two are below the horizontal plane, as illustrated in the second arrangement 322 of FIG. 3B. The two upper sources are used to obtain BB1 spectra and the two lower sources are used to obtain BB2 spectra. Since the upper and lower sources illuminate a region of the tissue sample using light incident to the region at different angles, an artifact—for example, or shadow—may affect one of the two reflectance spectra obtained for the region, while the other reflectance spectrum is unaffected. For example, during acquisition of spectral data, the BB1 spectrum may be unaffected by an artifact even if the BB2 spectrum is adversely affected by the artifact. In such a case, BB1 spectral data may be used to characterize the condition of the region of tissue even though the BB2 data is not representative of the region. In other embodiments, the BB1 and BB2 spectra comprise one or more other types of spectral data, such as absorbance spectra, adsorption spectra, transmission spectra, fluorescence spectra, and/or other types of optical and atomic emission spectra. The skilled artisan is aware of other ways in which BB1 and BB2 can be made to differ with respect to the ways in which tissue can be illuminated or otherwise contacted with electromagnetic radiation.

Figure 5A:
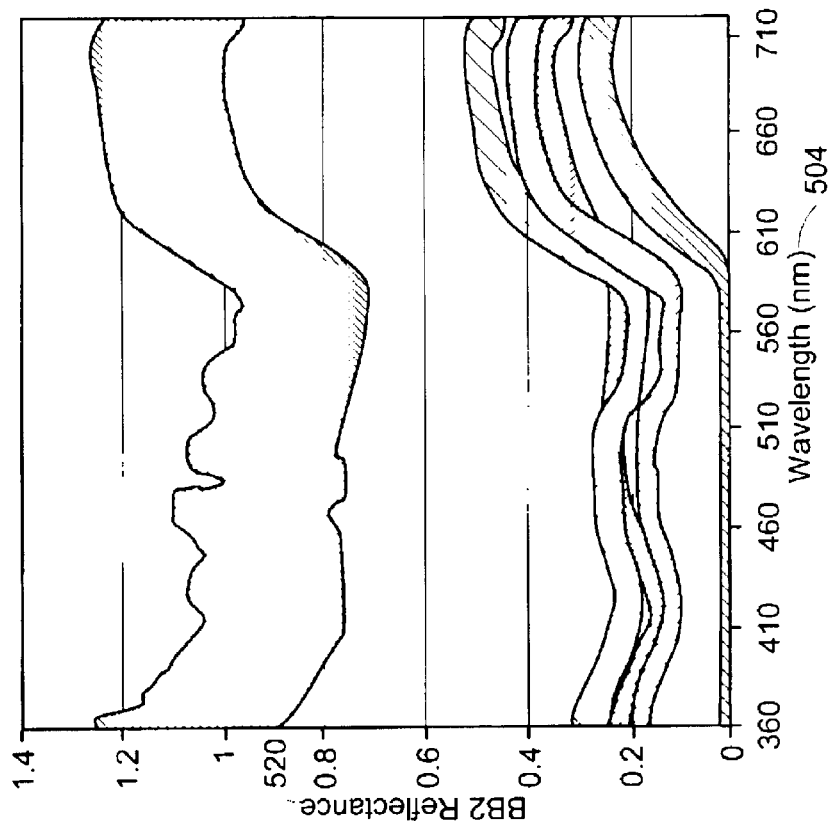
FIG. 5A shows a graph depicting mean values and standard deviations of broadband reflectance spectral data using the BB1 channel light source for regions confirmed as being obscured by blood, obscured by mucus, obscured by glare from the BB1 source, obscured by glare from the BB2 source, or unobscured, according to an illustrative embodiment of the invention.

FIG. 5A shows a graph depicting mean values and standard deviations of broadband reflectance spectral data using the BB1 channel light source for regions confirmed as being obscured by blood, obscured by mucus, obscured by glare from the BB1 source, obscured by glare from the BB2 source, or unobscured, according to an illustrative embodiment of the invention. Various sample test points corresponding to regions of tissue from patient scans were visually identified as having blood, mucus, or glare present. A sample point was identified as having blood present if it was completely covered by blood and if there was no glare. A sample point was identified as having mucus present if it was completely covered by mucus and if there was no glare. A sample point was identified as having glare based on visual evidence of glare and large reflectance values in at least one of the two sets of reflectance spectral data (the BB1 spectrum or the BB2 spectrum). FIG. 5A shows the range of BB1 reflectance values 502 for a given category of the sample test points which lie within one standard deviation of the mean for the category, plotted as a function of wavelength 504. FIG. 5A shows ranges of BB1 reflectance values 502 for each of the following categories of sample test points: those identified as having blood present 506, those identified as having mucus present 508, those identified as having glare from the BB1 illumination source 510, those identified as having glare from the BB2 illumination source 512, and those identified as unobstructed tissue 514.

Figure 5B:
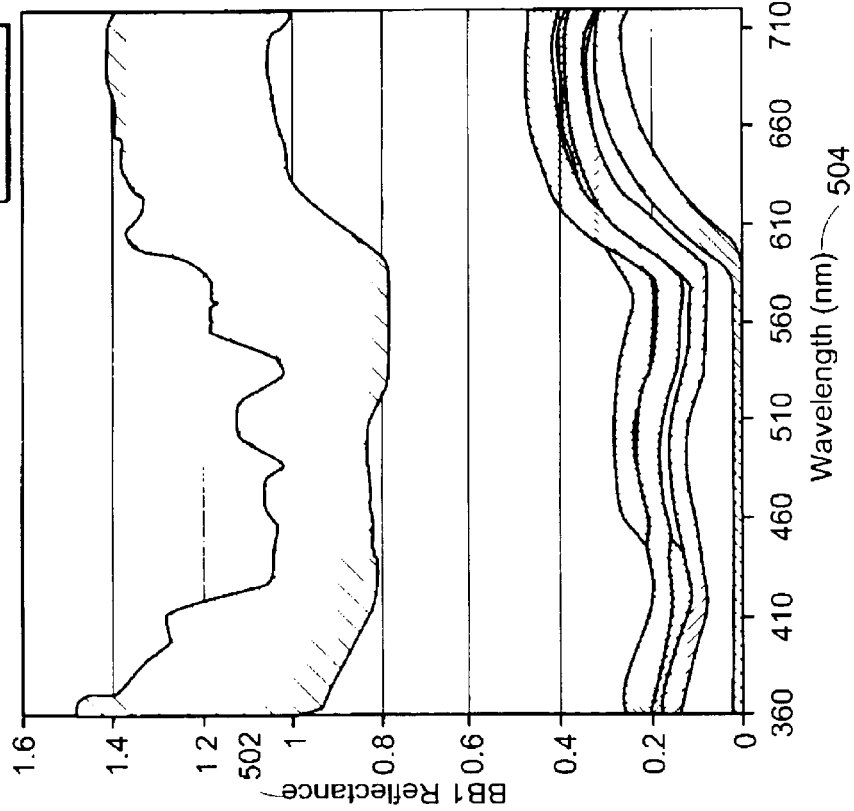
FIG. 5B shows a graph depicting mean values and standard deviations of broadband reflectance spectral data using the BB2 channel light source for regions confirmed as being obscured by blood, obscured by mucus, obscured by glare from the BB1 source, obscured by glare from the BB2 source, or unobscured, according to an illustrative embodiment of the invention.

Similarly, FIG. 5B shows a graph depicting mean values and standard deviations of broadband reflectance spectral data using the BB2 channel light source for regions confirmed as being obscured by blood 524, obscured by mucus 526, obscured by glare from the BB1 source 528, obscured by glare from the BB2 source 530, or unobscured 532, according to an illustrative embodiment of the invention. FIG. 5B shows the range of BB2 reflectance values 520 for a given category of the sample test points which lie within one standard deviation of the mean for the category, plotted as a function of wavelength 504. FIG. 5B shows ranges of BB2 reflectance values 520 for each of the following categories of sample test points: those identified as having blood present 524, those identified as having mucus present 526, those identified as having glare from the BB1 illumination source 528, those identified as having glare from the BB2 illumination source 530, and those identified as unobstructed tissue 532.

FIGS. 5A and 5B show that a region with glare from one illumination source does not necessarily have high reflectance values corresponding to data obtained using the other illumination source. For example, in FIG. 5A, the range of BB1 reflectance values 502 of points with visual evidence of glare from the BB2 source 512 is similar to the range of BB1 reflectance values 502 of unobstructed tissue 514. Similarly, in FIG. 5B, the range of BB2 reflectance values 520 of points demonstrating glare from the BB1 source 528 is similar to the range of BB2 reflectance values 520 of unobstructed tissue 532. Therefore, one of the two sets of reflectance spectral data may be useful in characterizing the tissue even if the other of the two sets is corrupted by an artifact, such as glare.

In one embodiment, it is desired to determine spectral characteristics caused by various artifacts so that data corresponding to a region affected by a given artifact may be identified. It is further desired to determine a spectral characteristic of an artifact based on the spectral data itself, without having to rely on other visual evidence of a given artifact. In order to determine these spectral characteristics, an embodiment of the invention comprises using spectral data known to be affected by a given artifact based on visual evidence, as well as spectral data known not to be affected by an artifact. Techniques that may be used to identify spectral characteristics and/or to develop classification rules determining whether given data are affected by an artifact include, for example, discriminant analysis (linear, nonlinear, multivariate), neural networks, principal component analysis, and decision tree analysis. One embodiment comprises determining a particular wavelength that gives the greatest difference between the artifact-affected spectral data (the outlier) and spectral data from corresponding nearby tissue that is known to be unaffected by the artifact (the tissue). Alternatively, the embodiment comprises determining a wavelength that gives the largest difference between the outlier and the tissue, as weighted by a measure of variability of the data. In one embodiment, this method locates where the difference between the mean reflectance for the outlier and the tissue is at a maximum relative to the difference between the standard deviations for the outlier data and the tissue data. In one embodiment, the method determines a maximum value of D as a function of wavelength, where D is the difference given in Equation 1 below:

$$D(\lambda) = \frac{|\mu(BB(\lambda))_{Outlier} - \mu(BB(\lambda))_{Tissue}|}{\sqrt{\sigma^2(BB(\lambda))_{Outlier} + \sigma^2(BB(\lambda))_{Tissue}}}, \quad (1)$$

where $\mu(BB(\lambda))_{outlier}$ is the mean of a set of reflectance spectral data at wavelength λ known to be affected by a given artifact, $\sigma(BB(\lambda))_{Tissue}$ is the mean of a set of reflectance spectral data at wavelength λ that is known not to be affected by the artifact, $\sigma(BB(\lambda))_{outlier}$ is the standard deviation of the set of reflectance spectral data at wavelength λknown to be affected by the given artifact, and $\sigma(BB(\lambda))_{Tissue}$ is the standard deviation of the set of reflectance spectral data at wavelength λ known not to be affected by the given artifact.

Figure 6A:
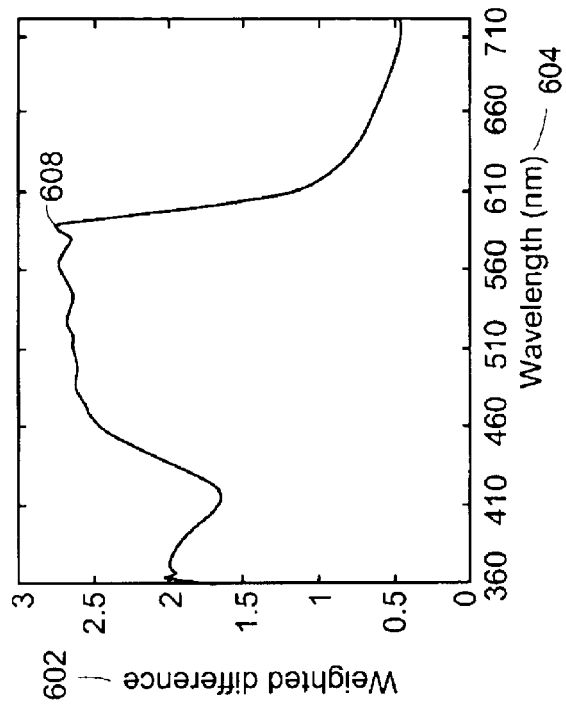
FIG. 6A shows a graph depicting the weighted difference between the mean reflectance values of glare-obscured regions and unobscured regions of tissue as a function of wavelength, according to an illustrative embodiment of the invention.

FIG. 6A shows a graph depicting the weighted difference 602 between the mean reflectance values of glare-obscured regions and unobscured regions of tissue as a function of wavelength 604, according to an illustrative embodiment of the invention. The weighted difference is as given in Equation 1. For the data sets used in FIG. 6A, the wavelength providing the maximum value 606 of D in Equation (1) is about 420 nm. Thus, exemplary spectral characteristics identifiable with this set of glare-obscured "outlier" data include the reflectance spectral data at around 420 nm, and any deviation of this data from reflectance spectral "tissue" data for unobscured regions of correspondingly similar tissue at around 420 nm. This embodiment uses reflectance spectral data. Other embodiments may use other types of spectral data, including fluorescence data.

Figure 6B:
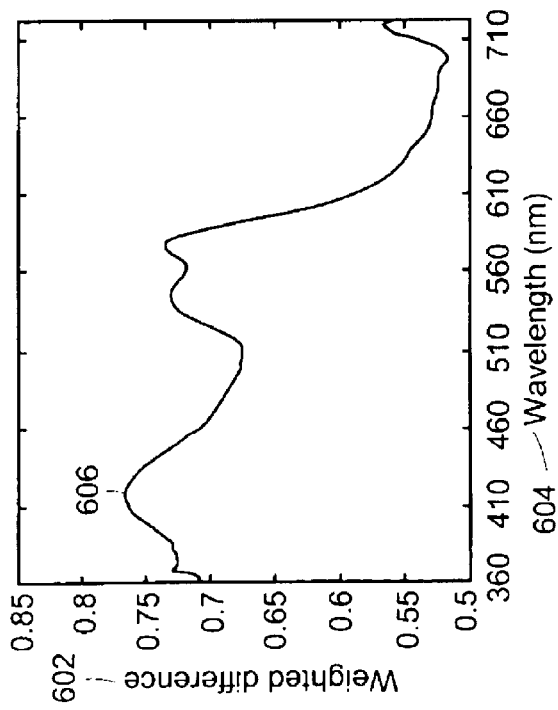
FIG. 6B shows a graph depicting the weighted difference between the mean reflectance values of blood-obscured regions and unobscured regions of tissue as a function of wavelength, according to an illustrative embodiment of the invention.

FIG. 6B shows a graph depicting the weighted difference 602 between the mean reflectance values of blood-obscured regions and unobscured regions of tissue as a function of wavelength 604, according to an illustrative embodiment of the invention. The weighted difference is as given in Equation 1. For the data sets used in FIG. 6B, the wavelength providing the maximum value 608 of D in Equation (1) is about 585 nm.

Thus, exemplary spectral characteristics identifiable with this set of blood-obscured "outlier" data include the reflectance spectral data at about 585 nm, and any deviation of this data from reflectance spectral "tissue" data for unobscured regions of correspondingly similar tissue at about 585 nm. This embodiment uses reflectance spectral data. Other embodiments may use other types of spectral data, including fluorescence spectral data.

Figure 6C:
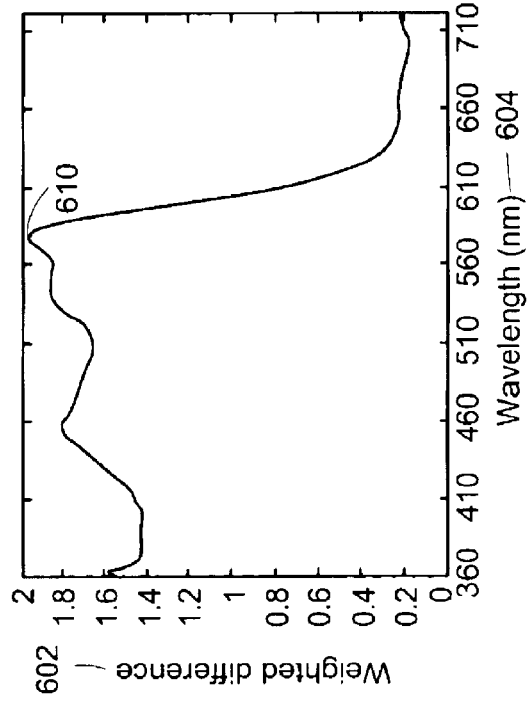
FIG. 6C shows a graph depicting the weighted difference between the mean reflectance values of mucus-obscured regions and unobscured regions of tissue as a function of wavelength, according to an illustrative embodiment of the invention.

FIG. 6C shows a graph depicting the weighted difference 602 between the mean reflectance values of mucus-obscured regions and unobscured regions of tissue as a function of wavelength 604, according to an illustrative embodiment of the invention. The weighted difference is as given in Equation 1. For the data sets used in FIG. 6C, the wavelength providing the maximum value 610 of D in Equation (1) is about 577 nm. Thus, exemplary spectral characteristics identifiable with this set of mucus-obscured "outlier" data include the reflectance spectral data at about 577 nm, and any deviation of this data from reflectance spectral "tissue" data for unobscured regions of correspondingly similar tissue at about 577 nm. This embodiment uses reflectance spectral data. Other embodiments may use other types of spectral data, including fluorescence spectral data.

In some embodiments, it may be desired to find a pair of wavelengths that would provide an acceptable spectral characteristic of an artifact "outlier." One illustrative embodiment comprises determining two wavelengths where the ratio of spectral data at the two wavelengths is most different for the artifact-affected spectral data (the "outlier") and spectral data from corresponding nearby tissue that is known to be unaffected by the artifact (the "tissue"). Alternatively, the method comprises determining two wavelengths where the ratio of spectral data at the two wavelengths weighted by a measure of variability is most different for the outlier data and the tissue data. In one embodiment, the method comprises determining a maximum value of D as a function of wavelength, where D is the difference given in Equation 2 below:

$$D = \frac{|\mu(BB(\lambda)/BB(\lambda'))_{Outlier} - \mu(BB(\lambda)/BB(\lambda'))_{Tissue}|}{\sqrt{\sigma^2(BB(\lambda)/BB(\lambda'))_{Outlier} + \sigma^2(BB(\lambda)/BB(\lambda'))_{Tissue}}}, \quad (2)$$

where $\mu(BB(\lambda)/BB(\lambda'))_{Outlier}$ is the mean of the ratios of reflectance at wavelength λ and reflectance at wavelength λ' for a set of reflectance spectral data known to be affected by a given artifact, $\mu(BB(\lambda)/BB(\lambda'))_{Tissue}$ is the mean of the ratios of reflectance at wavelength λ and reflectance at wavelength λ' for a set of reflectance spectral data that is known not to be affected by the given artifact, $\sigma(BB(\lambda)/BB(\lambda'))_{Outlier}$ is the standard deviation of the ratios of reflectance at wavelength λ and reflectance at wavelength λ' for a set of reflectance spectral data known to be affected by the given artifact, and $\sigma(BB(\lambda)/BB(\lambda'))_{Tissue}$ is the standard deviation of the ratios of reflectance at wavelength λ and reflectance at wavelength λ' for a set of reflectance spectral data known not to be affected by the given artifact.

Figure 7A:
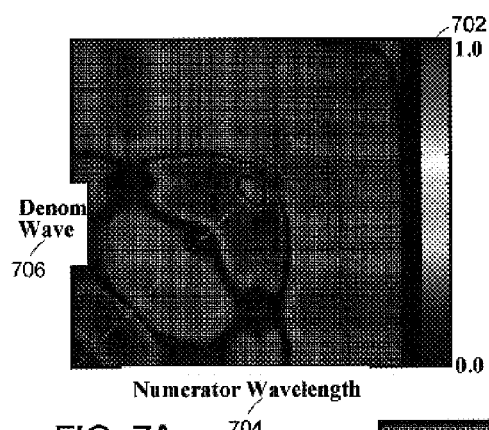
FIG. 7A shows a graph depicting a ratio of the weighted differences between the mean reflectance values of glare-obscured regions and unobscured regions of tissue at two wavelengths, according to an illustrative embodiment of the invention.

FIG. 7A shows a graph depicting a ratio of the weighted differences 702 between the mean reflectance values of glare-obscured regions and unobscured regions of tissue at two wavelengths, a numerator wavelength 704 and a denominator wavelength 706, according to an illustrative embodiment of the invention. The weighted difference 702 is as given in Equation 2. For the data sets used in FIG. 7A, the two wavelengths providing the maximum value of D in Equation (2) are about 401 nm (numerator) and about 404 nm (denominator). Thus, exemplary spectral characteristics identifiable with this set of glare-obscured "outlier" data include the ratio of reflectance spectral data at about 401 nm and the reflectance spectral data at about 404 nm, as well as any deviation of this ratio from those of corresponding regions of similar but unobscured tissue. This embodiment uses reflectance spectral data. Other embodiments may use other types of spectral data, including fluorescence data.

Figure 7B:
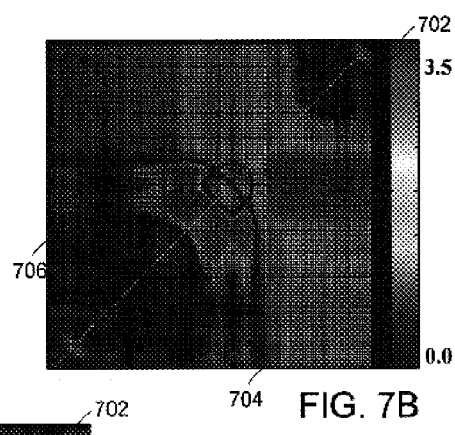
FIG. 7B shows a graph depicting a ratio of the weighted differences between the mean reflectance values of blood-obscured regions and unobscured regions of tissue at two wavelengths, according to an illustrative embodiment of the invention.

FIG. 7B shows a graph depicting a ratio of the weighted differences 702 between the mean reflectance values of blood-obscured regions and unobscured regions of tissue at two wavelengths, a numerator wavelength 704 and a denominator wavelength 706, according to an illustrative embodiment of the invention. The weighted difference is as given in Equation 2. For the data sets used in FIG. 7B, the two wavelengths providing the maximum value of D in Equation (2) are about 595 nm (numerator) and about 718 nm (denominator). Thus, an exemplary spectral characteristic identifiable with this set of blood-obscured "outlier" data includes the ratio of the reflectance spectral data at about 595 nm and the reflectance spectral data about 718 nm. This embodiment uses reflectance spectral data. Other embodiments may use other types of spectral data, including fluorescence data.

Figure 7C:
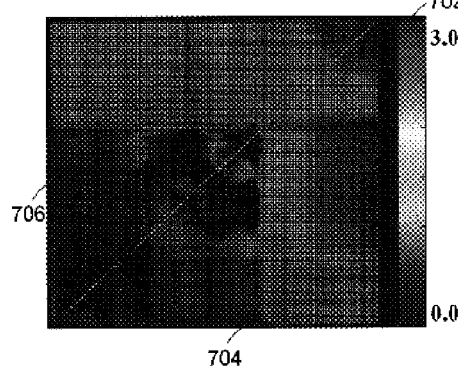
FIG. 7C shows a graph depicting a ratio of the weighted differences between the mean reflectance values of mucus-obscured regions and unobscured regions of tissue at two wavelengths, according to an illustrative embodiment of the invention.

FIG. 7C shows a graph depicting a ratio of the weighted differences 702 between the mean reflectance values of mucus-obscured regions and unobscured regions of tissue at two wavelengths, a numerator wavelength 704 and a denominator wavelength 706, according to an illustrative embodiment of the invention. The weighted difference is as given in Equation 2. For the data sets used in FIG. 7B, the two wavelengths providing the maximum value of D in Equation (2) are about 545 nm (numerator) and about 533 nm (denominator). Thus, an exemplary spectral characteristic identifiable with this set of mucus-obscured "outlier" data includes the ratio of the reflectance spectral data at about 545 nm and the reflectance spectral data at about 533 nm. This embodiment uses reflectance spectral data. Other embodiments may use other types of spectral data, including fluorescence data.

Another type of lighting artifact which may obscure spectral data is shadow, which may be caused, for example, by an obstruction blocking part of the light from an illumination source on the optical probe 104 of the embodiment apparatus. It may be important to differentiate between glare and shadow, so that spectral data representing unobstructed tissue can be properly identified. In an embodiment, broadband reflectance is expressed as the intensity of light diffusely reflected from a region of the tissue, $I_r$, over the intensity of incident light, $I_o$, at the region. When glare is measured in addition to light diffusely reflected from the tissue, a percentage of the original intensity of incident light is included in the tissue reflectance measurement, so that the "reflectance" reading of a region of a sample experiencing glare, $R_g(\lambda)$, may be expressed as in Equation 3:

$$R_g(\lambda) = (I_r(\lambda) + \alpha I_o(\lambda))/I_o(\lambda), \quad (3)$$

where $\alpha$ is a real number between 0.0 and 1.0; $I_r(\lambda)$ is the intensity of light diffusely reflected from the region of tissue at wavelength $\lambda$, and $I_o(\lambda)$ is the intensity of light incident on the region of the sample at wavelength $\lambda$. The intensity of the specularly-reflected light is $\alpha I_o(\lambda)$. When the region of the sample is shadowed, only a portion of the incident intensity reaches the region. Thus, the "reflectance" reading of a region of a sample experiencing shadow, $R_s(\lambda)$ may be expressed as in Equation 4:

$$R_s(\lambda) = \beta I_r(\lambda)/I_o(\lambda). \quad (4)$$

where $\beta$ is a real number between 0.0 and 1.0; $I_r(\lambda)$ is the intensity of light at wavelength $\lambda$ diffusely reflected from the region of tissue with an incident light intensity of $I_o(\lambda)$, and $I_o(\lambda)$ is the intensity of light at wavelength $\lambda$ that would be incident on the region of the sample if unshadowed.

In one embodiment of the invention, the method comprises determining if only one set of a pair of sets of spectral data is affected by a lighting artifact, such as glare or shadow, each set having been obtained using light incident on the sample at a unique angle. If it is determined that only one set of a pair of sets of spectral data is affected by the artifact, then the other set of spectral data may be used in the determination of a characteristic of the region of the sample, for example. In one embodiment, it is determined that there is evidence of a lighting artifact in the spectral data. Such evidence may be a large difference between the reflectance measurements of the two sets of spectral data. If such evidence exists, then one of the reflectance measurements will either be $R_g$ or $R_s$, as given by Equation 3 and Equation 4. In cases where members of only one set are affected by a lighting artifact, the remaining set of reflectance measurements may be expressed as R, the intensity of light diffusely reflected from the region of the tissue, $I_r$, divided by the intensity of light incident on the region of the tissue, $I_o$. In an embodiment method, the larger of the two reflectance measurements corresponding to a given wavelength is divided by the smaller. In cases where only one of the sets is affected by a lighting artifact, the resulting quotient will be either $R_g/R$, which is equal to $1 + \alpha I_o(\lambda)/I_r(\lambda)$ or $R/R_s$, which is equal to the constant, $1/\beta$. glare is present, the value of the quotient will depend on wavelength and the plot of the quotient as a function of wavelength should look like an inverted unobstructed tissue broadband signal because of the $\alpha I_o(\lambda)/I_r(\lambda)$ term. If shadow is present, the plot of the quotient should be constant across the spectrum.

FIG. 8 shows a graph depicting as a function of wavelength 804 mean values and confidence intervals of a ratio 802 of BB1 and BB2 broadband reflectance spectral values (larger value divided by smaller value) for regions confirmed as being either glare-obscured or shadow-obscured tissue, according to an illustrative embodiment of the invention. The shadow points 806 yield a nearly constant value, while the glare points 808 vary over the range of wavelength 804 in a manner that resembles the inverse of unobstructed tissue reflectance. Thus, FIG. 8 illustrates an embodiment in which it is determined whether only one set of a pair of sets of spectral data is affected by either glare or shadow, such that the other set is unaffected by glare or shadow and may be used to determine a characteristic of the tissue, for example. In an embodiment, the method comprises differentiating between glare and shadow by observing the steep slope of glare-affected reflectance spectral measurements between about 577 nm and 599 nm, for example, compared to the nearly flat slope of shadow-affected reflectance spectral measurements at those wavelengths, as seen in FIG. 8.

In one embodiment, the method comprises developing spectral artifact classification rules (metrics) using spectral data, including one or more sets of fluorescence and broadband reflectance data obtained using light at one or more angles. In one embodiment, one set of fluorescence data and two sets of reflectance data are used for a given region of a tissue sample, where each of the two sets of reflectance data are obtained using light incident on the region at a different angle. These metrics determine what data is representative of a given region of tissue. By varying the metrics, desired levels of sensitivity and selectivity of a resulting tissue characterization using tissue-representative data may be achieved.

The following metrics for an exemplary preferred embodiment were determined using the embodiments discussed above, as well as other techniques. These metrics were developed using one set of fluorescence data and two sets of reflectance data, BB1 and BB2, for samples of cervical tissue. Other embodiments use other combinations of spectral data sets. Each of the two sets of reflectance data used in the following metrics were obtained using light incident to a region of a sample at different angles. An embodiment of the invention uses any or all of the metrics listed below to determine if any set of data should be eliminated from use in determining a characteristic of a region of tissue, due to the presence of a spectral artifact. In an embodiment of the invention, wavelengths within a range of the wavelengths shown below are used. In one embodiment, this range about the wavelengths is about ±10 nm. In an embodiment of the invention, only certain parts of the metrics shown below are used. In one embodiment, only a portion of a given set of spectral data are eliminated, not the entire set. In one embodiment, BB1 and BB2 reflectance data are obtained, but fluorescence data is not. Here, "eliminate data" means to eliminate data from consideration in an analysis, for example, an analysis to determine a condition of a region. It is possible to change sensitivity and selectivity of a tissue diagnostic algorithm by varying the metrics below, for instance by changing one or more of the threshold constants. Such variations are within an embodiment of this invention. The metrics for the exemplary preferred embodiment are as follows:

Glare Metric #1: Eliminate BB1 data IF:

| | I. | BB1(419) > 0.25 OR BB1(499)/BB1(543) < 1.05; |
|---|---|---|
| OR | II. | Max {|ΔBB|/avgBB}(370–710) > 0.25 AND BB1(419) > 0.18; |
| OR | III. | Max{|ΔBB|/avgBB}(370–710) > 0.4 AND {BB1(576)/BB2(576)}/{BB1(599)/BB2(599)} > 1.1 AND BB2(699) > 0.3. |

Glare Metric #2: Eliminate BB2 data IF:

| | I. | BB2(419) > 0.25 OR BB2(499)/BB2(543) < 1.05; |
|---|---|---|
| OR | II. | Max{|ΔBB|/avgBB}(370–710) > 0.25 AND BB2(419) > 0.18; |
| OR | III. | Max{|ΔBB|/avgBB}(370–710) > 0.4 AND {BB2(576)/BB1(576)}/{BB2(599)/BB1(599)} > 1.1 AND BB1(699) > 0.3. |

Shadow Metric #1: Eliminate BB1 data IF:

| | I. | BB2(499) > BB1(499) AND Max{|ΔBB|/avgBB}(370–710) > 0.25 AND BB1(499) < 0.05; |
|---|---|---|
| OR | II. | Max{|ΔBB|/avgBB}(370–710) > 0.5 AND {BB2(576)/BB1(576)}/{BB2(599)/BB1(599)} < 1.1 AND BB2 > BB1 AND BB2(419) < 0.2. |

Shadow Metric #2: Eliminate BB2 data IF:

| | I. | BB1(499) > BB2(499) AND Max{|ΔBB|/avgBB}(370–710) > 0.25 AND BB2(499) < 0.05; |
|---|---|---|
| OR | II. | Max{|ΔBB|/avgBB}(370–710) > 0.5 AND {BB1(576)/BB2(576)}/{BB1(599)/BB2(599)} < 1.1 AND BB1 > BB2 AND BB1(419) < 0.2. |

Low Signal: Eliminate BB1, BB2, and F1 data IF:

| | I. | F1(479) < 3.5 counts/μJ; |
|---|---|---|
| OR | II. | BB1(499) < 0.035 & BB2(499) < 0.035. |

Mucus Metric: Eliminate BB1, BB2, and F1 data IF:

| | I. | Max{|ΔBB|/avgBB}(370–710) < 0.25 AND avgBB(577) > 0.11; |
|---|---|---|
| AND | II. | BB1(406)/BB1(541) < 1.0 AND BB2(406)/BB2(535) < 1.0; |
| AND | III. | BB1(544)/BB1(532) > 0.95 AND BB2(544)/BB2(532) > 0.95. | where BB1 (X) is the BB1 reflectance spectrum measurement at wavelength X, BB2 (X) is the BB2 reflectance spectrum measurement at wavelength X, Max{|ΔBB1/avgBB}(370–710) indicates the maximum of {the absolute value of the difference between the BB1 and BB2 reflectance spectrum measurements divided by the average of the BB1 and BB2 measurements at a given wavelength} over the range of about 370 to 710 nm, and F1 (X) is the fluorescence spectrum measurement at wavelength X. The following are notes regarding the Metrics listed above and apply to a preferred embodiment, subject to the variations described above:

Glare Metric #1 and Glare Metric #2:
Level I: Broadband measurements are generally greater than about 0.25 at about 419 nm only when there is glare in the channel (i.e. BB1 or BB2 ). The lack of a downward slope between about 499 and about 543 nm is also a strong indication that the broadband measurements are affected by glare.
Level II: Large percentage differences in the broadband measurements combined with higher than average reflectance at about 419 nm also indicates the presence of glare.
Level III: A maximum broadband percent difference that is larger than about 0.4 indicates that there is a lighting artifact present. The presence of a slope when the broadband measurements at about 576 and about 599 nm are divided and an off-channel broadband greater than about 0.3 at about 699 nm reveals that the lighting artifact is due to glare instead of shadow.
If a point is identified as glare in one channel, then subsequently identified as glare in both channels, both broadband measurements should be eliminated.

Shadow Metric #1 and Shadow Metric #2:
Level I: Broadband measurements that are shadowed generally will have a large percent difference between BB1 and BB2 and a low reflectance at about 499 nm.
Level II: A maximum broadband percent difference that is larger than about 0.5 indicates that there is a lighting artifact present. Lacking a large slope when the broadband measurements at about 576 and about 599 nm are divided and an off-channel broadband less than about 0.2 at about 419 nm reveals that the point is shadow instead of glare.
Cases where both BB and F1 measurements should be eliminated:

Low Signal:
Broadband measurements lower than about 0.035 at about 449 nm or fluorescence measurements lower than about 3.5 at about 479 nm indicate that the measurements are not coming from tissue, but rather from blood, the Os, smoke tube, speculum, or another obstruction. Sites with significant shadowing in both broadband channels are also identified with this metric. Because of the uncertainty of the tissue being measured, the reflectance and fluorescence data from that point are assumed invalid, regardless of whether it was identified by fluorescence or the broadband channels.

Mucus Metric:
Level I: Mucus broadband measurements generally will have a lower percent difference than glare, and a greater average reflectance than (unobstructed) tissue.
Level II: The shape of the mucus broadband curves can help to identify a point as mucus. A smaller change in the broadband measurements between about 406 nm and about 541 nm indicates a smaller hemoglobin β-band and therefore a greater chance of the observed point being mucus.
Level III: A smaller change from about 532 nm to about 544 nm is also an indication of a smaller hemoglobin β-band, and helps to differentiate mucus from glare.
Points that are obstructed by mucus will give inaccurate readings for fluorescence and both broadband reflectance channels.

The metrics used in this embodiment include a low signal metric, which detects spectral data affected by obstruction artifacts such as blood, a speculum, a smoke tube, or other obstruction. These were combined into one low signal metric in this embodiment, since regions affected by these artifacts exhibit similar characteristics, such as low fluorescence and low broadband reflectance measurements.

FIG. 9A shows a graph depicting broadband reflectance 902 as a function of wavelength 904 for the BB1 channel 906 and the BB2 channel 908 measurements for a region of tissue where the BB1 data is affected by glare but the BB2 data is not, according to an illustrative embodiment of the invention. The glare leads to a higher 110 value of reflectance 902 than that of surrounding unaffected tissue. By applying the metrics listed above according to an embodiment of this invention, it is determined that the BB1 set of spectral data is affected by glare and is thus not suitably representative of this region of the tissue sample. Applying the method of this embodiment also determines that the BB2 set of spectral data is representative of this region of the sample (unaffected by an artifact), since it is not eliminated. One embodiment comprises using this representative data to determine a condition of this region of the sample, for example, the state of health.

FIG. 9B shows a graph depicting broadband reflectance 902 as a function of wavelength 904 for the BB1 channel 910 and the BB2 channel 912 broadband reflectance spectral data for a region of tissue where the BB2 data is affected by shadow but the BB1 data is not, according to an illustrative embodiment of the invention. The shadow leads to a lower value of reflectance 902 than that of surrounding unaffected tissue. By applying the metrics listed above in this embodiment, it is determined that the BB2 set of spectral data is affected by shadow and is therefore not suitably representative of this region of the tissue sample. However, applying this method also leads to the determination that the BB1 set of spectral data is representative of this region of the sample, since the BB1 set of data is not eliminated. One embodiment comprises using this representative data to determine a condition of this region of the sample, for example, the state of health.

Figures 9C, 9D:
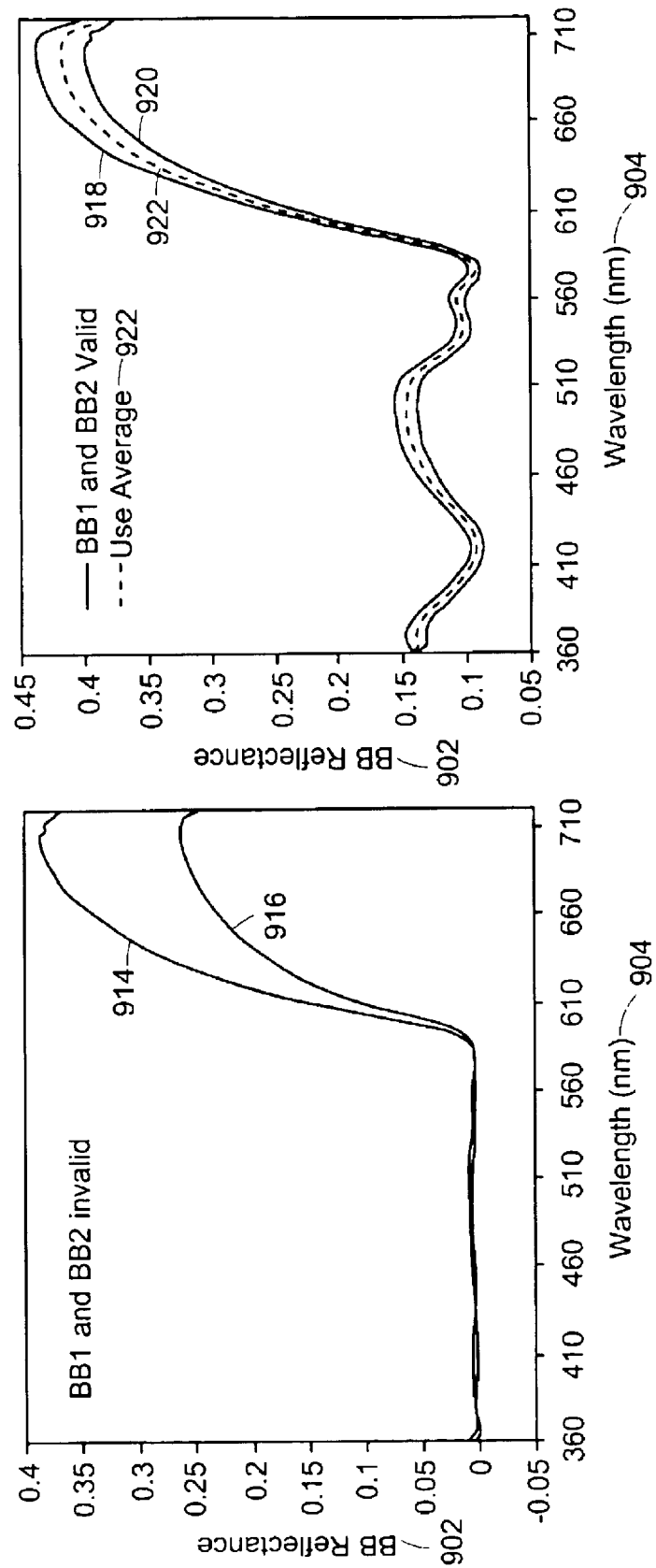
FIG. 9C shows a graph depicting BB1 and BB2 broadband reflectance spectral data for a region of tissue that is obscured by blood, according to an illustrative embodiment of the invention.
FIG. 9D shows a graph depicting BB1 and BB2 broadband reflectance spectral data for a region of tissue that is unobscured, according to an illustrative embodiment of the invention.

FIG. 9C shows a graph depicting broadband reflectance 902 as a function of wavelength 904 for the BB1 channel 914 and the BB2 channel 916 measurements for a region of tissue that is obscured by blood, according to an illustrative embodiment of the invention. By applying the metrics listed above, it is determined that blood is present, and that both the BB1 and the BB2 sets of spectral data are considered unrepresentative of this region of the tissue sample.

FIG. 9D shows a graph depicting broadband reflectance 902 as a function of wavelength 904 for the BB1 channel 918 and the BB2 channel 920 measurements for a region of tissue that is unobscured, according to an illustrative embodiment of the invention. Applying this method determines that neither set of spectral data is affected by an artifact, and, therefore, either is representative of the tissue sample. One embodiment comprises using an average value 922 of the BB1 and BB2 measurements at each wavelength to represent the region of the tissue sample in determining a condition of this region, for example, the state of health of the region.

Application of the metrics listed above was performed using various tissue types to verify the sensitivity and specificity of the metrics. While it is undesirable in preferred embodiments to eliminate good spectral data of normal tissue, it is worse in preferred embodiments to eliminate good spectral data of diseased tissue, particularly if it is desired to use the data in the classification of the state of health of a region of tissue. The following tissue types were used in the verification: tt-132 (metaplasia by impression), tt-155 (normal by impression), tt-115 (mucus), tt-117 (blood), and NEDpath (no evidence of disease confirmed by pathology), and cin 23 all (CIN II/CIN III diseased tissue). Table 1 shows the number of points (regions) corresponding to each of these tissue types, the determinations from the metrics listed above for these points, and the number of points where one set of broadband reflectance spectral data were eliminated, where both sets of broadband reflectance spectral data were eliminated, and where both reflectance and fluorescence spectral data were eliminated.

TABLE 1

Verification of Metrics

| Tissue Type | cin23all | nedpath | tt-115 | tt-117 | tt-132 | tt-155 |
| --- | --- | --- | --- | --- | --- | --- |
| Total pts. | 230 | 460 | 584 | 26 | 3909 | 1356 |
| Low Signal | 2 | 4 | 10 | 16 | 2 | 1 |
| Mucus | 0 | 3 (2) | 85 | 0 | 5 | 0 |
| Glare in BB1 | 5 | 21 | 19 | 0 | 115 | 11 |
| Glare in BB2 | 4 | 22 | 9 | 2 | 113 | 20 |
| Glare in both | 6 | 5 | 42 | 1 | 45 | 3 |
| Shadow in BB1 | 17 | 10 | 7 | 2 | 165 | 46 |
| Shadow in BB2 | 6 | 24 (1) | 44 | 0 | 291 | 30 |
| One BB Removed | 32 (13.9%) | 77 (16.7%) | 79 (13.5%) | 4 (15.4%) | 685 (17.5%) | 107 (1.3%) |
| Both RB Removed | 8 (3.5%) | 12 (2.6%) | 137 (23.5%) | 17 (65.4%) | 52 (1.3%) | 3 (0.2%) |
| Fl and BB Removed | 2 (0.9%) | 7 (1.5%) | 95 (16.27%) | 16 (61.5%) | 7 (0.18%) | 1 (0.07%) |

For the regions (points) corresponding to CIN II/CIN III diseased tissue, no broadband reflectance measurements were unnecessarily eliminated from the set. The points identified as being low signal were all located on the Os. All points that were identified by the metric as glare or shadow were verified as being correct.

For the nedpath points (no evidence of disease), only two tissue points were unnecessarily eliminated after being misidentified as mucus. A point that was actually dark red tissue with glare was incorrectly identified as shadow in BB2 . The points that were identified as glare were verified as being correct.

Out of the 584 mucus points, 85 were correctly identified as mucus. The points that were identified as glare or shadow (and mucus) were verified as being correct.

Out of the 26 blood points, 16 were identified as being low signal. The glare points and shadow points were accurate.

Out of the 3909 points in the metaplasia by impression group, there were no valid tissue points lost. The data set was improved by eliminating over 700 readings of points affected by either glare or shadow.

Out of the 1358 normal by impression points, no measurements were unnecessarily removed from the set.

Figures 10A, 10B:
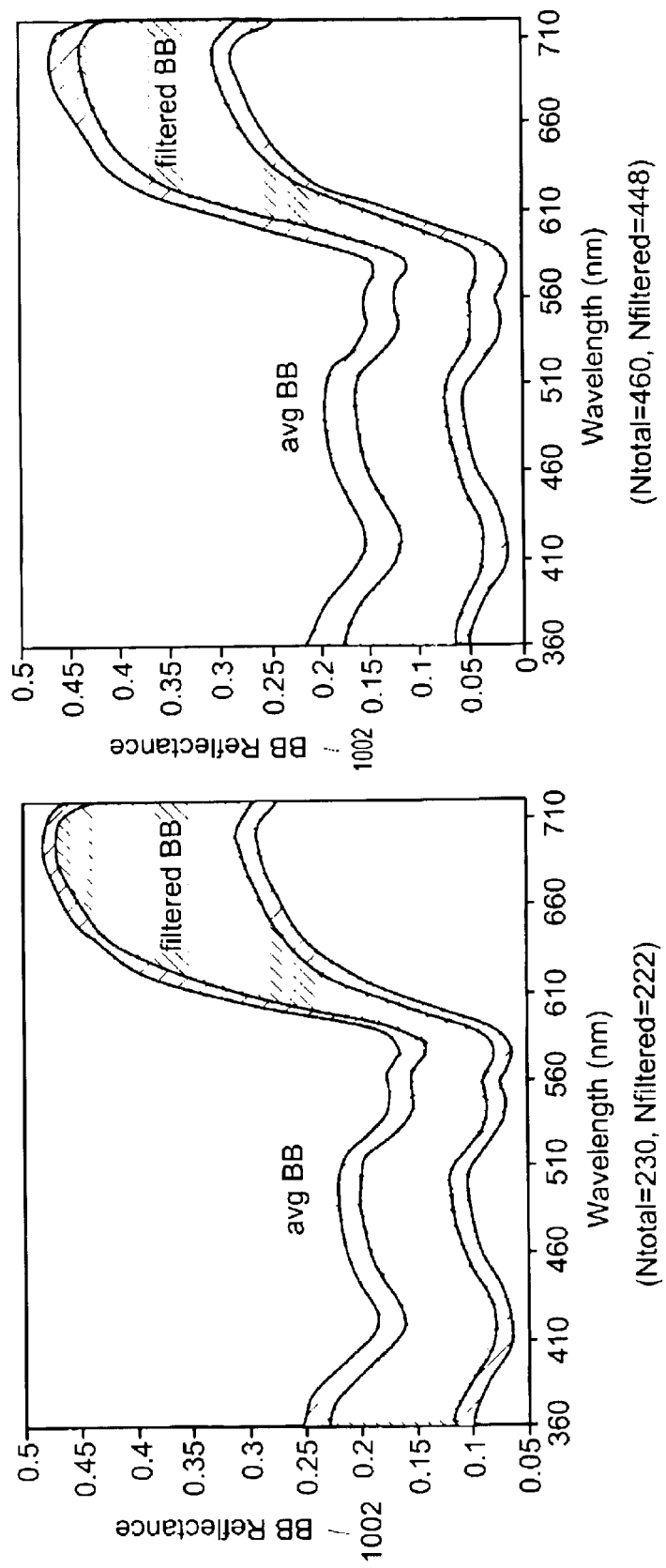
FIG. 10A shows a graph depicting the reduction in the variability of broadband reflectance measurements of CIN II/III-confirmed tissue produced by filtering, according to an illustrative embodiment of the invention.
FIG. 10B shows a graph depicting the reduction in the variability of broadband reflectance measurements of tissue classified as "no evidence of disease confirmed by pathology" produced by filtering, according to an illustrative embodiment of the invention.

FIG. 10A shows a graph depicting the reduction in the variability of broadband reflectance measurements 1002 of CIN II/III-confirmed tissue produced by filtering (eliminating non-representative spectral data) using the metrics described above, according to an illustrative embodiment of the invention. The graph depicts mean values and standard deviations of broadband reflectance spectral data before and after filtering.

FIG. 10B shows a graph depicting the reduction in the variability of broadband reflectance measurements 1002 of tissue classified as "no evidence of disease confirmed by pathology" produced by filtering using the metrics described above, according to an illustrative embodiment of the invention. The graph depicts mean values and standard deviations of broadband reflectance spectral data before and after filtering.

Figures 10C, 10D:
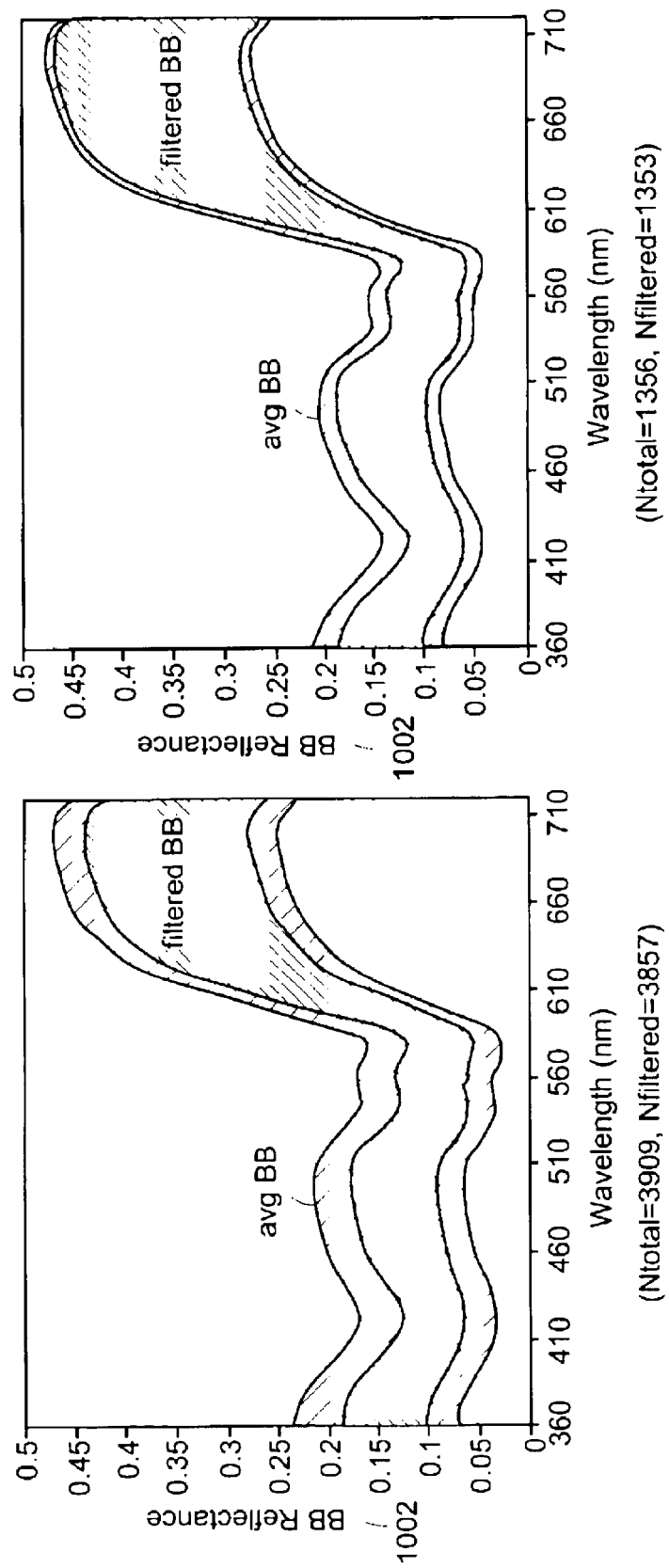
FIG. 10C shows a graph depicting the reduction in the variability of broadband reflectance measurements of tissue classified as "metaplasia by impression" produced by filtering, according to an illustrative embodiment of the invention.
FIG. 10D shows a graph depicting the reduction in the variability of broadband reflectance measurements of tissue classified as "normal by impression" produced by filtering, according to an illustrative embodiment of the invention.

FIG. 10C shows a graph depicting the reduction in the variability of broadband reflectance measurements 1002 of tissue classified as "metaplasia by impression" produced by filtering using the metrics described above, according to an illustrative embodiment of the invention. The graph depicts mean values and standard deviations of broadband reflectance spectral data before and after filtering.

FIG. 10D shows a graph depicting the reduction in the variability of broadband reflectance measurements 1002 of tissue classified as "normal by impression" produced by filtering using the metrics described above, according to an illustrative embodiment of the invention. The graph depicts mean values and standard deviations of broadband reflectance spectral data before and after filtering.

Figures 11A, 11B:
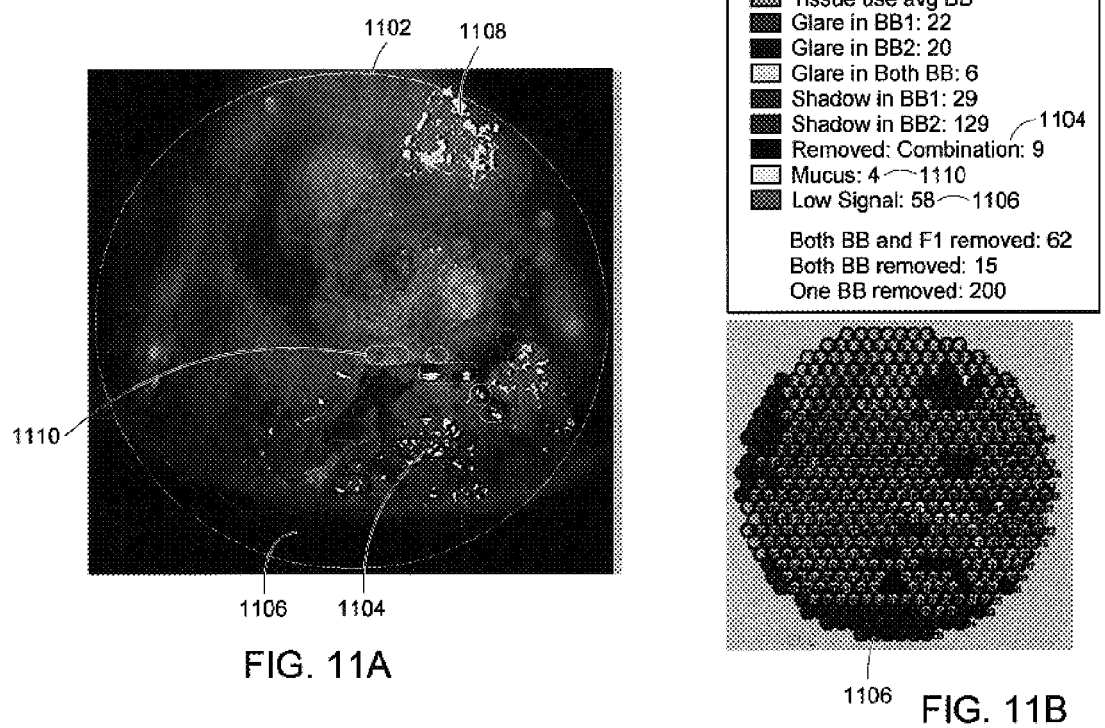
FIG. 11A depicts an exemplary image of cervical tissue divided into regions for which two types of reflectance spectral data and one type of fluorescence spectral data are obtained, according to an illustrative embodiment of the invention.
FIG. 11B is a representation of the regions depicted in FIG. 11A and shows the categorization of each region according to an illustrative embodiment of the invention.

FIG. 11A depicts an exemplary image of cervical tissue 1102 divided into regions for which two types of reflectance spectral data and one type of fluorescence spectral data are obtained, according to an illustrative embodiment of the invention. FIG. 11B is a representation of the regions depicted in FIG. 11A and shows the categorization of each region according to an illustrative embodiment of the invention. The black-highlighted sections 1104 of the image 1102 in FIG. 11A correspond to points (regions) that had both reflectance measurements eliminated by application of the embodiment method. Many of the lower points 1106, as seen in both FIGS. 11A and 11B, are in shadow because the speculum obstructs the view of one of the channels. Glare is correctly identified prominently at the upper one o'clock position 1108. Since there are blood points on the shadowed section, some are labeled blood (low signal) and others are treated as shadow. The mucus metric identifies several points 1110 around the Os that have a bubbly, mucus-like liquid.

FIG. 12A depicts an exemplary image of cervical tissue 1202 divided into regions for which two types of reflectance spectral data and one type of fluorescence spectral data are obtained, according to an illustrative embodiment of the invention. FIG. 12B is a representation of the regions depicted in FIG. 12B and shows the categorization of each region according to an illustrative embodiment of the invention. FIGS. 12A and 12B show an example of a cervix that has a large portion of the lower half 1204 affected by shadow. However, only one of the sets of reflectance spectral data (BB2 ) is affected by the shadow artifact. The BB1 reflectance spectral data is not affected by shadow. Applying the metrics above, the BB1 data are used to describe these regions, while the BB2 data are eliminated from consideration. The accuracy of the reflectance measurements should be improved significantly for this patient using the metrics of the embodiment discussed above, since the more accurate broadband measurements will be used instead of simply averaging the two broadband measurements, which would skew the measurements due to a lighting artifact.

FIG. 13A depicts an exemplary image of cervical tissue 1302 divided into regions for which two types of reflectance spectral data and one type of fluorescence spectral data are obtained, according to an illustrative embodiment of the invention. FIG. 13B is a representation of the regions depicted in FIG. 13A and shows the categorization of each region according to an illustrative embodiment of the invention. FIGS. 13A and 13B show an image with a portion 1304 that is shadowed and off of the cervix. Due to an obstruction from the smoke tube in the upper part of the image, there are many low signals. Even though much of the cervix is shadowed in BB1 1306, there are still some usable BB2 and fluorescence readings.

FIG. 14A depicts an exemplary image of cervical tissue 1402 divided into regions for which two types of reflectance spectral data and one type of fluorescence spectral data are obtained, according to an illustrative embodiment of the invention. FIG. 14B is a representation of the regions depicted in FIG. 14A and shows the categorization of each region according to an illustrative embodiment of the invention. The image in FIG. 14A shows a large mucus obstruction 1404. The metrics of the embodiment do a good job of identifying mucus that is thick and light colored. The metrics correctly mark the dark red tissue as tissue instead of blood or shadow. The top edge of the cervix is identified as shadow, and glare points are correctly flagged.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of determining whether spectral data obtained from a region of a tissue sample are affected by an artifact, said method comprising the steps of:
   obtaining a first set of spectral data corresponding to a region of a tissue sample using light incident to said region at a first angle;
   obtaining a second set of spectral data corresponding to said region using light incident to said region at a second angle; and
   determining whether said first set of data is affected by an artifact based at least in part on a subset of said first set of data and a subset of said second set of data.

2. The method of claim 1, wherein said first set of spectral data comprises reflectance spectral data and said second set of spectral data comprises reflectance spectral data.

3. The method of claim 1, further comprising obtaining a third set of spectral data, where said third set of spectral data comprises fluorescence spectral data.

4. The method of claim 1, wherein said determining step comprises computing a difference between $R_1$, a member of said first set of spectral data, and $R_2$, a member of said second set of spectral data, and comparing said difference to a constant, where $R_1$ and $R_2$ correspond to at least approximately identical wavelengths.

5. The method of claim 4, wherein said difference is a percent difference.

6. The method of claim 1, wherein said determining step comprises computing N differences, $|R_1(X_i)-R_2(X_i)|$, optionally weighting each of said differences using at least one of $R_1(X_i)$ and $R_2(X_i)$, defining a maximum of a subset of said N optionally-weighted differences, and comparing said maximum to a first constant, where i=1 to N, N is an integer, $X_i$ is a wavelength between about 360 nm and about 720 nm, $R_1(X_i)$ is a member of said first set of data corresponding to said wavelength $X_i$, and $R_2(X_i)$ is a member of said second set of data corresponding to said wavelength $X_i$.

7. The method of claim 6, wherein said determining step further comprises comparing $R_1(X_1)$ to a second constant, where $R_1(X_1)$ is a member of said first set of data corresponding to a wavelength $X_1$ between about 409 nm and about 429 nm.

8. The method of claim 6, wherein said determining step further comprises comparing a value Q to a second constant, where Q is an approximate slope of a plot of $\{R_1(X_i)/R_2(X_i)\}$ with respect to wavelength, over a subset of a wavelength range of about 360 nm to about 720 nm.

9. The method of claim 6, wherein said determining step further comprises comparing $R_1(X_1)$ to a second constant and comparing $R_1(X_1)$ to $R_2(X_1)$, where $R_1(X_1)$ is a member of said first set of data corresponding to a wavelength $X_1$ between about 360 nm and about 720 nm, and $R_2(X_1)$ is a member of said second set of data corresponding to said wavelength $X_1$.

10. The method of claim 6, wherein said determining step further comprises comparing $R_1(X_1)$ to a second constant and comparing $R_1(X_1)$ to $R_2(X_1)$, where $R_1(X_1)$ is a member of said first set of data corresponding to a wavelength $X_1$ between about 489 nm and about 509 nm, and $R_2(X_1)$ is a member of said second set of data corresponding to said wavelength $X_1$.

11. The method of claim 1, wherein said determining step comprises comparing $R_1(X_1)$ to a constant, where $R_1(X_1)$ is a member of said first set of data corresponding to a wavelength $X_1$ between about 409 nm and about 429 nm.

12. The method of claim 11, wherein said determining step further comprises comparing a value Q to a second constant, where said value Q is an approximate slope of a plot of $\{R_1(X_i)/R_2(X_i)\}$ with respect to wavelength, over a subset of a wavelength range of about 576 nm to about 599 nm.

13. The method of claim 1, wherein said determining step comprises comparing the quotient $R_1(X_1)/R_1(X_2)$ to a constant, where $R_1(X_1)$ is a member of said first set of data corresponding to a wavelength $X_1$ between about 360 nm and about 720 nm, and $R_1(X_2)$ is a member of said first set of data corresponding to a wavelength $X_2$ between about 360 nm and about 720 nm.

14. The method of claim 13 wherein $X_1$ is a wavelength between about 489 nm and 509 nm and $X_2$ is a wavelength between about 533 nm and about 553 nm.

15. The method of claim 6, wherein said determining step further comprises comparing the quotient $\{(R_1(X_1)/R_2(X_1))/(R_1(X_2)/R_2(X_2))\}$ to a second constant, where $X_1$ is a wavelength between about 360 nm and about 720 nm, $X_2$ is a wavelength between about 360 nm and about 720 nm, $R_1(X_1)$ is a member of said first set of data corresponding to said wavelength $X_1$, $R_2(X_1)$ is a member of said second set of data corresponding to said wavelength $X_1$, $R_1(X_2)$ is a member of said first set of data corresponding to said wavelength $X_2$, $R_2(X_2)$ is a member of said second set of data corresponding to said wavelength $X_2$.

16. The method of claim 15 wherein $X_1$ is a wavelength between about 566 nm and about 586 nm, and $X_2$ is a wavelength between about 589 nm and about 609 nm.

17. The method of claim 16, wherein said determining step further comprises comparing $R_1(X_3)$ to a third constant, where $R_1(X_3)$ is a member of said first set of data corresponding to a wavelength $X_3$ between about 689 and about 709 nm.

18. The method of claim 15, wherein said determining step further comprises comparing $R_1(X_3)$ to a third constant, where $R_1(X_3)$ is a member of said first set of data corresponding to a wavelength $X_3$ between about 360 nm and about 720 nm.

19. The method of claim 15, wherein said determining step further comprises comparing $R_1(X_3)$ to a third constant, where $R_1(X_3)$ is a member of said first set of data corresponding to a wavelength $X_3$ between about 409 nm and about 429 nm.

20. The method of claim 1, wherein said determining step comprises comparing $R_1$ to a first constant and comparing $R_2$ to a second constant, where $R_1$ is a member of said first set of data corresponding to a wavelength between about 489 nm and about 509 nm and $R_2$ is a member of said second set of data corresponding to a wavelength between about 489 nm and about 509 nm.

21. The method of claim 1, wherein said artifact comprises a lighting artifact.

22. The method of claim 21, wherein said lighting artifact comprises glare.

23. The method of claim 21, wherein said lighting artifact comprises shadow.

24. The method of claim 1, wherein said artifact comprises an obstruction.

25. The method of claim 24, wherein said obstruction comprises blood.

26. The method of claim 24, wherein said obstruction comprises a portion of at least one of a group consisting of a speculum and a smoke tube.

27. The method of claim 24, wherein said obstruction comprises mucus.

28. The method of claim 1, wherein said tissue sample comprises cervical tissue.

29. The method of claim 1, wherein said tissue sample comprises epithelial cells.

30. The method of claim 1, wherein said tissue sample comprises at least one of a group consisting of colorectal, gastroesophageal, urinary bladder, lung, and skin tissue.

31. A method of determining whether spectral data corresponding to a region of a tissue sample is affected by an artifact, said method comprising the steps of:
   obtaining a first set of reflectance spectral data corresponding to a region of a tissue sample using light incident to said region at a first angle;
   obtaining a second set of reflectance spectral data corresponding to said region using light incident to said region at a second angle;
   obtaining a set of fluorescence spectral data corresponding to said region; and
   determining whether any of said first set of reflectance spectral data, said second set of reflectance spectral data and said set of fluorescence spectral data are affected by an artifact based at least in part on at least one of the following: a subset of said first set of reflectance spectral data, a subset of said second set of reflectance spectral data, and a subset of said set of fluorescence spectral data.

32. The method of claim 31, wherein said determining step comprises comparing F to a constant, where F is a member of said set of fluorescence spectral data corresponding to a wavelength between about 469 nm and about 489 nm.

33. A method of determining a spectral characteristic of an artifact, said method comprising the steps of:
   (a) at each of a first plurality of regions of tissue, obtaining a first set of reflectance spectral data affected by a known artifact;
   (b) at each of a second plurality of regions of tissue, obtaining a second set of reflectance spectral data not affected by said known artifact; and
   (c) determining a spectral characteristic of said known artifact based at least in part on said first set of spectral data and said second set of spectral data.

34. The method of claim 33, wherein said determining step comprises locating a wavelength at which there is a maximum difference between a mean of one or more members of said first set corresponding to said wavelength and a mean of one or more members of said second set corresponding to said wavelength, relative to a variation measure.

35. The method of claim 33, wherein said determining step comprises computing N differences, $|\mu_i(A_j(X_i))-\mu_i(B_k(X_i))|$, and defining a maximum of a subset of said N differences, where i=1 to N, N is an integer, $X_1$ is a wavelength between about 360 nm and about 720 nm, j=1 to M1, M1 is an integer, $A_j(X_i)$ represents one of M1 members of said first set of reflectance spectral data corresponding to said wavelength $X_i$, k=1 to M2, M2 is an integer, $B_k(X_i)$ represents one of M2 members of said second set of reflectance spectral data corresponding to said wavelength $X_i$, $\mu_i(A_j(X_i))$ is a mean of said M1 members of said first set of data corresponding to said wavelength $X_i$, and $\mu_i(B_k(X_i))$ is a mean of said M2 members of said second set of data corresponding to said wavelength $X_i$.

36. The method of claim 33, wherein said determining step comprises computing N quotients, $[|\mu_i(A_j(X_i))-\mu_i(B_k(X_i))|/\{\sigma_i^2(A_j(X_i))+\sigma_i^2(B_k))x_i\}^{0.5}]$, and defining a maximum of a subset of said N quotients, where i=1 to N, N is an integer, $X_i$ is a wavelength between about 360 nm and about 720 nm, j=1 to M1, M1 is an integer, $A_j(X_i)$ represents one of M1 members of said first set of reflectance spectral data corresponding to said wavelength $X_i$, k=1 to M2, M2 is an integer, $B_k(X_i)$ represents one of M2 members of said second set of reflectance spectral data corresponding to said wavelength $X_i$, $\mu_i(A_j(X_i))$ is a mean of said M1 members of said first set of data corresponding to said wavelength $X_i$, $\mu_i(B_k(X_i))$ is a mean of said M2 members of said second set of data corresponding to said wavelength $X_i$, $\sigma_i(A_j(X_i))$ represents a standard deviation of said M1 members of said first set of data corresponding to said wavelength $X_i$, and $\sigma_i(B_k(X_i))$ represents a standard deviation of said M2 members of said second set of data corresponding to said wavelength $X_i$.

37. The method of claim 33, wherein said determining step comprises computing N quotients, $[|\mu_i(A_j(X1_i)/A_j(X2_i))-\mu_i(B_k(X1_i)/B_k(X2_i))|/\{\sigma_i^2(B_k(X1_i)/B_k(X2_i))\}^{.5}]$, and defining a maximum of a subset of said N quotients, where i=1 to N, N is an integer, $X1_i$ is a wavelength between about 360 nm and about 720 nm, $X2_i$ is a wavelength between about 360 nm and about 720 nm, j=1 to M1, M1 is an integer, $A_j(X1_i)$ represents one of M1 members of said first set of reflectance spectral data corresponding to said wavelength $X1_i$, $A_j(X2_i)$ represents one of M1 members of said first set of reflectance spectral data corresponding to said wavelength $X2_i$, k=1 to M2, M2 is an integer, $B_k(X1_i)$ represents one of M2 members of said second set of reflectance spectral data corresponding to said wavelength $X1_i$, $B_k(X2_i)$ represents one of M2 members of said second set of reflectance spectral data corresponding to said wavelength $X2_i$, $\mu_i(A_j(X1_i)/A_j(X2_i))$ is a mean of M1 quotients $A_j(X1_i)/A_j(X2_i)$ for j=1 to M1, $\mu_i(B_k(X1_i)/B_k(X2_i))$ is a mean of M2 quotients $B_k(X1_i)/B_k(X2_i)$ for k=1 to M2, $\sigma_i(A_j(X1_i)/A_j(X2_i))$ represents a standard deviation of said M1 quotients $A_j(X1_i)/A_j(X2_i)$, and $\sigma_i(B_k(X1_i)/B_k(X2_i))$ represents a standard deviation of said M2 quotients $B_k(X1_i)/B_k(X2_i)$.

38. A method of determining a characteristic of a region of a tissue sample, said method comprising the steps of:

(a) obtaining a first set of reflectance spectral data corresponding to a region of a tissue sample using light incident to said region at a first angle;

(b) obtaining a second set of reflectance spectral data corresponding to said region using light incident to said region at a second angle;

(c) determining whether at least one of said first set of reflectance data and said second set of reflectance data is affected by an artifact based at least in part on a subset of said first set of reflectance data and a subset of said second set of reflectance data;

(d) rejecting at least one member of at least one of said first set of reflectance data and said second set of reflectance data determined in step (c) to be affected by said artifact; and (e) determining a characteristic of said region of said tissue sample based at least in part on at least one member of at least one of said first set of reflectance data and said second set of reflectance data not rejected in step (d).

39. The method of claim 33, further comprising obtaining a set of fluorescence spectral data corresponding to said region, and wherein step (e) comprises determining said condition of said region of said tissue sample based at least in part on at least one member of at least one of said first set of reflectance data and said second set of reflectance data and at least one member of said set of fluorescence spectral data.

* * * * *